(12) United States Patent
Shichi et al.

(10) Patent No.: US 7,326,942 B2
(45) Date of Patent: Feb. 5, 2008

(54) ION BEAM SYSTEM AND MACHINING METHOD

(75) Inventors: Hiroyasu Shichi, Tokyo (JP);
Muneyuki Fukuda, Kokubunji (JP);
Yoshinori Nakayama, Sayama (JP);
Masaki Hasegawa, Sayama (JP);
Satoshi Tomimatsu, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 320 days.

(21) Appl. No.: 11/210,732

(22) Filed: Aug. 25, 2005

(65) Prior Publication Data
US 2006/0065854 A1   Mar. 30, 2006

(30) Foreign Application Priority Data
Sep. 29, 2004   (JP)   .............................. 2004-283011
Jun. 8, 2005    (JP)   .............................. 2005-167670

(51) Int. Cl.
*H01J 37/30*   (2006.01)
*H01J 37/305*  (2006.01)
*H01J 37/08*   (2006.01)

(52) U.S. Cl. .............................. 250/492.21; 250/492.2; 250/492.22; 250/492.3

(58) Field of Classification Search ...................... None
See application file for complete search history.

(56) References Cited

U.S. PATENT DOCUMENTS 6,538,254 B1   3/2003   Tomimatsa et al.

7,154,106 B2 *  12/2006  Oi et al.  .................. 250/492.3

FOREIGN PATENT DOCUMENTS

| JP | 07-320670 | 12/1995 |
| JP | 2000-156393 | 6/2000 |
| JP | 2002-148159 | 5/2002 |
| JP | 2002-150990 | 5/2002 |
| JP | 2003-311435 | 11/2003 |
| JP | 2004-309499 | 11/2004 |
| JP | 2005-010014 | 1/2005 |
| WO | WO 99/05506 | 2/1999 |

* cited by examiner

*Primary Examiner*—Nikita Wells
(74) *Attorney, Agent, or Firm*—Antonelli, Terry, Stout & Kraus, LLP.

(57) ABSTRACT

There is a machining method which shortens a cross-section forming time by an ion beam, a machining method which shortens a machining time for separating a micro sample from a wafer, and an ion beam machining system. The ion beam machining system has a vacuum container containing a duoplasmatron, non-axially symmetric ion beam lens and stencil mask, wherein a micro sample is removed from a sample by an argon ion beam having a steep beam profile in a direction perpendicular to the cross-section. The cross-section observations for wafer inspection/defect analysis used in device manufacture can be obtained in a short time. Further, there is a inspection/analysis method which does not cause defects even if a sample is removed and a wafer is returned to the process.

16 Claims, 20 Drawing Sheets

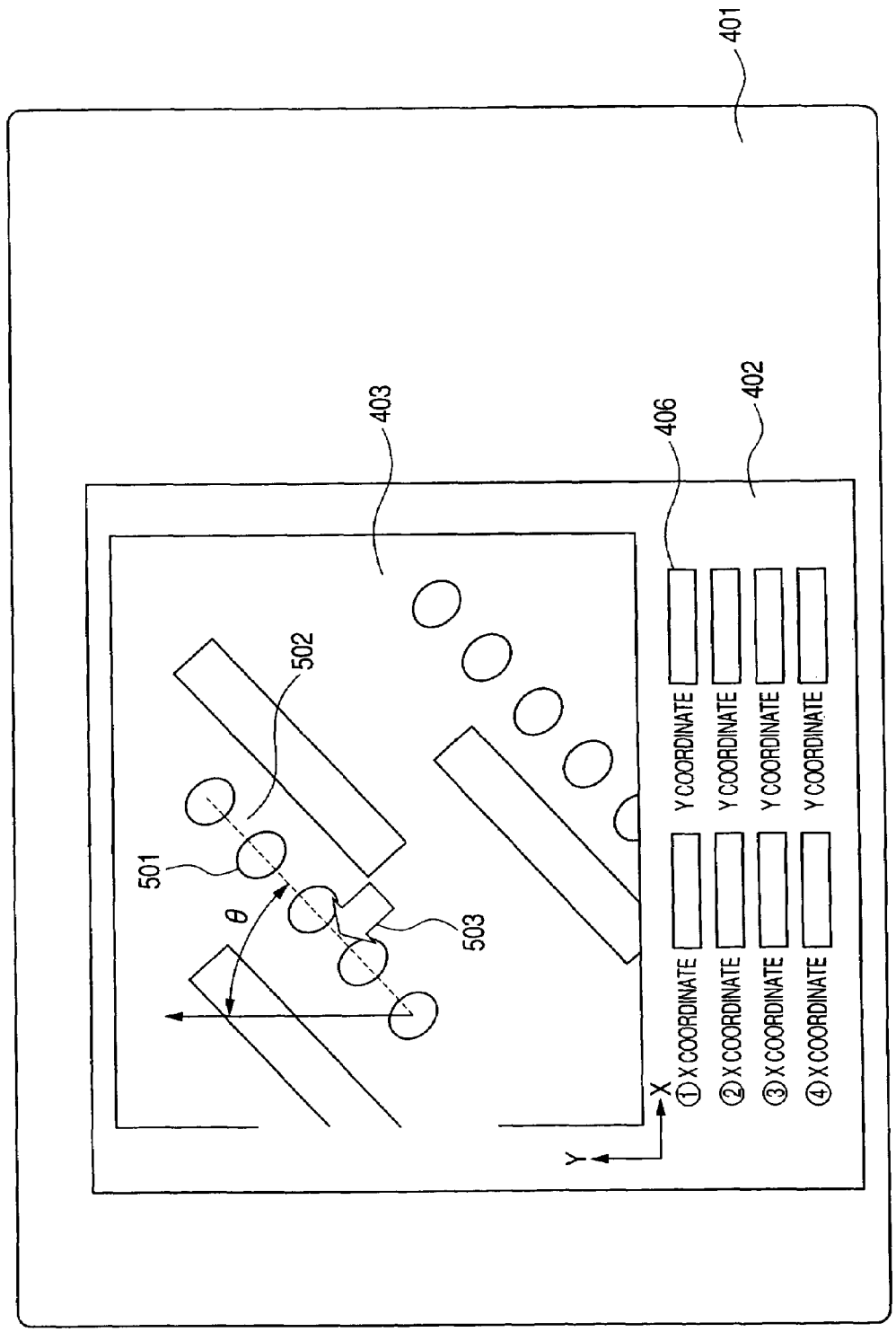

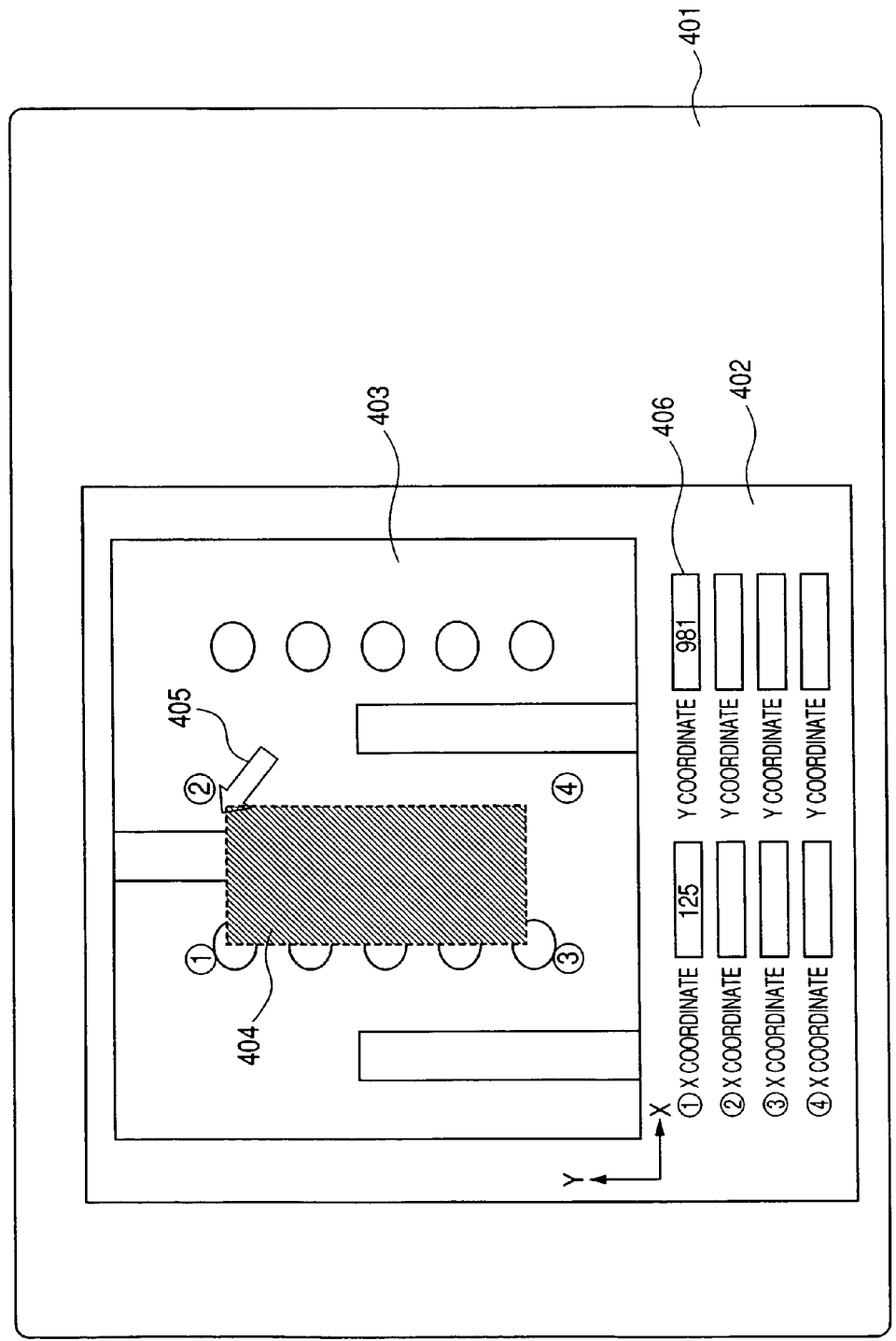

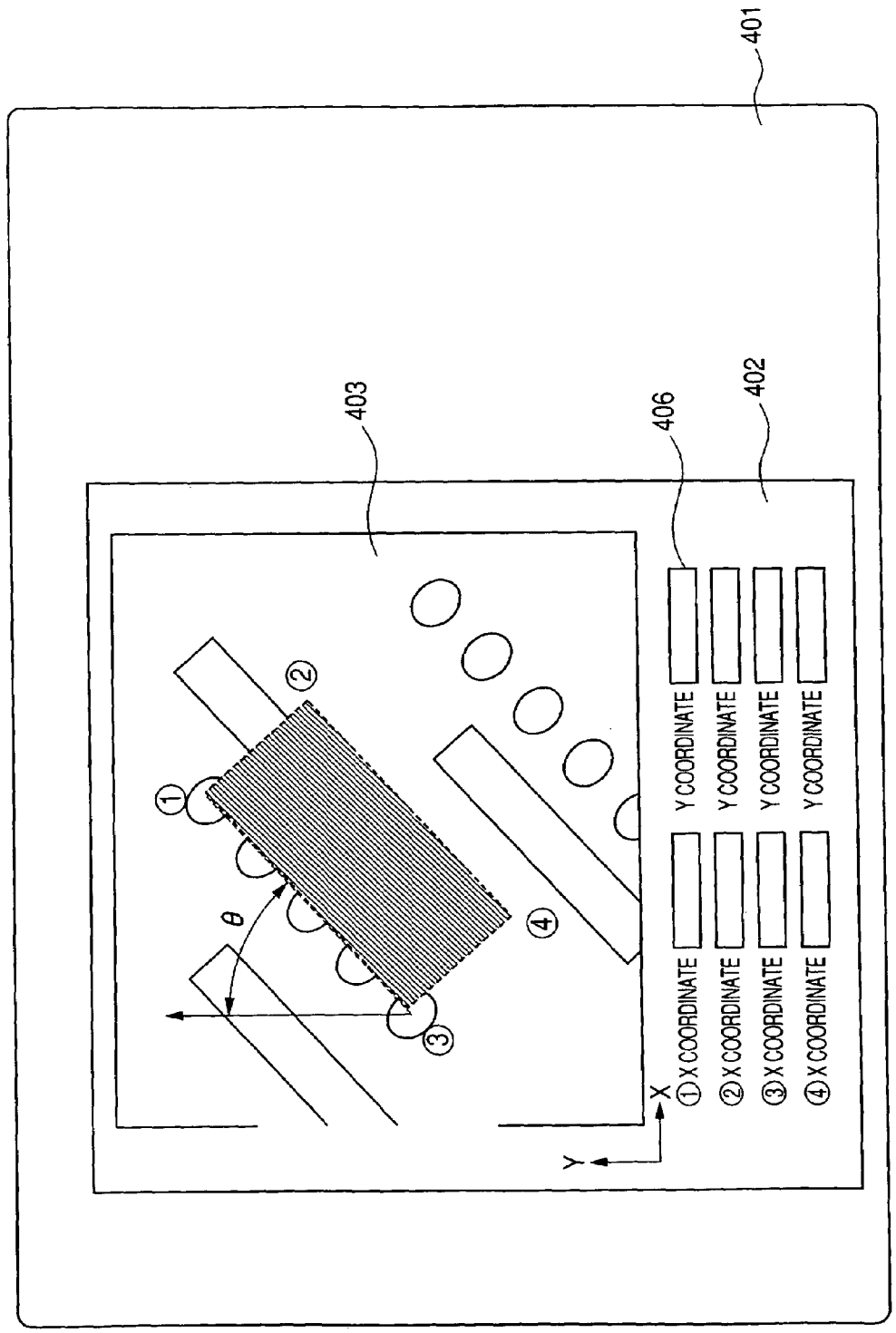

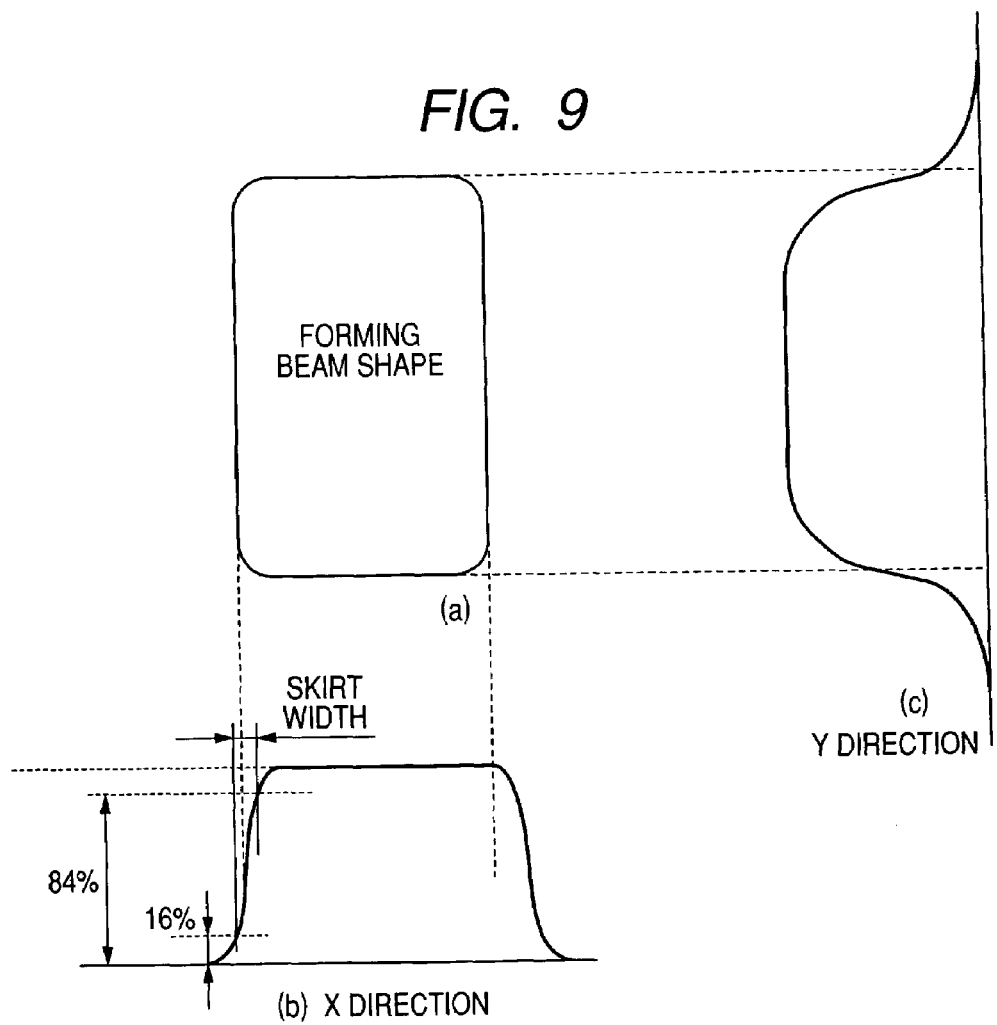
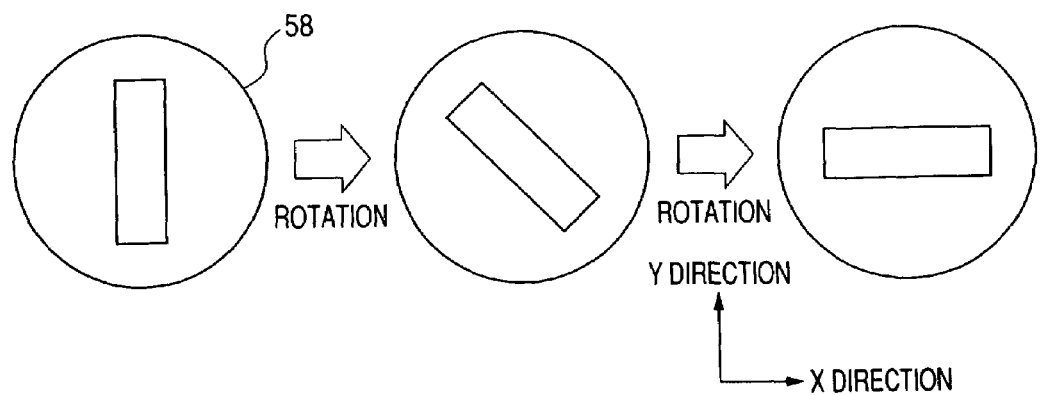

TOP VIEW

FRONT VIEW

SIDE VIEW

FIG. 15A
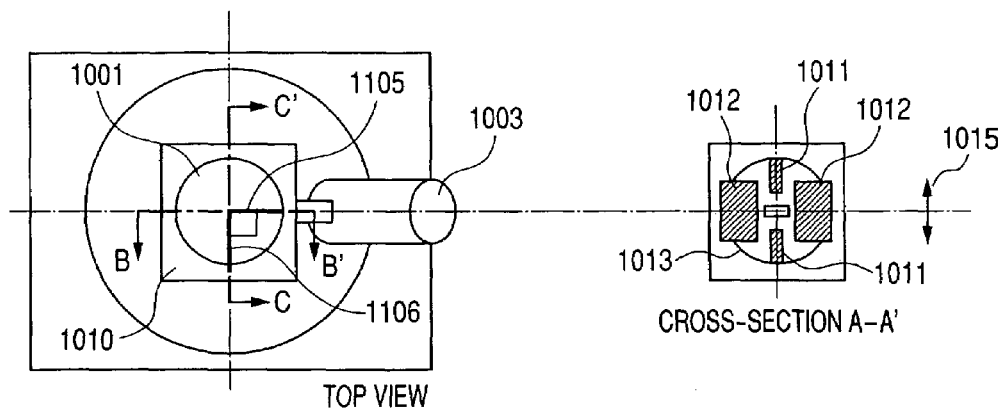
TOP VIEW
CROSS-SECTION A-A'
FIG. 15B
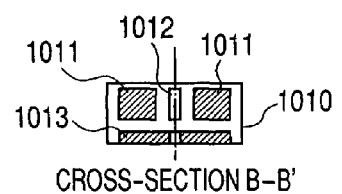
CROSS-SECTION B-B'
FIG. 15C
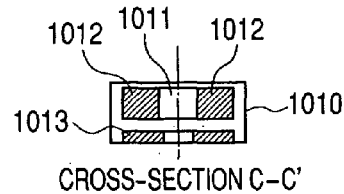
CROSS-SECTION C-C'
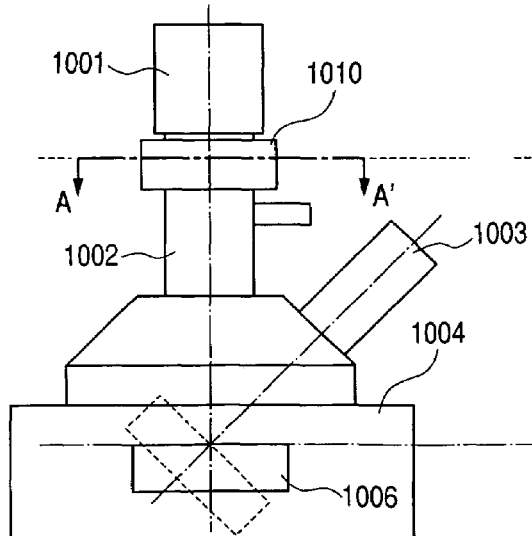
FRONT VIEW
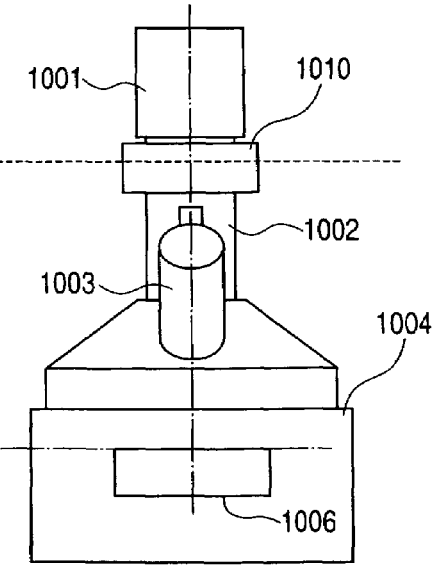
SIDE VIEW

TOP VIEW

FRONT VIEW

SIDE VIEW

TOP VIEW

FRONT VIEW

SIDE VIEW

ION BEAM SYSTEM AND MACHINING METHOD

CLAIM OF PRIORITY

The present application claims priority from Japanese applications JP 2004-283011, filed on Sep. 29, 2004 and JP 2005-167670 filed on Jun. 8, 2005, the contents of which are hereby incorporated by reference into this application.

FIELD OF THE INVENTION

This invention relates to a method of inspecting/analyzing of electronic components such as semiconductor devices, an electronic component manufacturing method, a method of machining a sample cross-section by an ion beam, a method of machining a sample which separates or prepares separation of a micro sample from the sample, and an ion beam system.

BACKGROUND OF THE INVENTION

High yield manufacture is called for in the manufacture of electronic components, such as semiconductor devices, e.g., semiconductor memories like dynamic random-access memories, microprocessors and semiconductor lasers, and magnetic heads. This is because a fall of product yield leads to lower profits. Therefore, early detection of and measures needed to deal with defects, foreign matter and poor machining are major issues. For example, in electronic component manufacturing plants, much effort is expended on discovery of defects by careful inspection, and analysis of their cause. In actual electronic component manufacturing processes using wafers, the wafers in the course of being processed are examined, the cause of abnormalities such as defects and foreign matter in circuit patterns is investigated, and methods to deal with them are considered.

Usually, a scanning electron microscope (SEM: Scanning Electron Microscope, hereafter SEM) of super-resolution capacity is used for observation of sample abnormalities. In recent years, composite FIB-SEM devices which combine SEM and FIB (Focused Ion Beams) have also come to be used. With this FIB-SEM device, SEM observation of a cross-section can be performed by irradiating a FIB and forming rectangular holes in a desired part.

In JP-A No. 150990/2002, "Micro Sample Machining Observation Method and Device", a device which observes and analyzes defects and foreign matter by forming rectangular holes near the abnormal spot of a sample by FIB, and observes the cross-section of these rectangular holes by a SEM device, is disclosed.

In international publication WO99/05506, "Sample Manufacturing Method and Device", a technique of extracting a micro sample for TEM observation from a bulk sample by using FIB and a probe, is disclosed.

In JP-A No. 156393/2000, "Electronic Component Manufacturing Method", a technique for removing a micro sample for inspection from a wafer without splitting the wafer, and returning the wafer after taking out the micro sample to the production line, is disclosed. In the invention disclosed in this document, the progress of the machining process is monitored by a monitor, and the wafer is inspected and analyzed.

In JP-A No. 320670/1995, "Processing Method and Device Using a Focused Ion Beam", a technique using a helicon wave ion source for machining a sample for SEM observation by an argon ion beam with a beam spot diameter of 0.1 μm, is disclosed.

[Patent document 1] JP-A No. 150990/2002
[Patent document 2] International publication WO99/05506
[Patent document 3] JP-A No. 156393/2000
[Patent document 4] JP-A 320670/1995

SUMMARY OF THE INVENTION

In a machining technique to form a cross-section by an ion beam, or a technique for separating a micro sample from a sample by an ion beam, and observing the micro sample with an electron microscope, the following problems remain.

In the defect analysis of electronic components, such as semiconductor memories and microprocessors, it is strongly desired to perform plural analyses simultaneously and feedback the analysis results in a short time. Specifically, it is important from the viewpoint of reducing manufacturing cost to extract and prepare an analysis sample as early as possible from a discovered faulty point, to conduct inspection and analysis, and to promptly feed back the obtained results to the manufacturing process. At present, about 5 to 10 minutes is required to form a cross-section by an ion beam, and about 30 to 60 minutes is required to extract a micro sample by an ion beam, but this is not short enough for production line requirements, and shortening of the time required to prepare an observation/analysis sample from a (larger) sample is a current problem.

In the case of prior ion beam machining, an ion beam with a circular beam spot is used. When using a circular beam, the precision of machining a sample cross-section is determined by the beam diameter (curvature of ion beam spot).

The machining time by the ion beam is effectively inversely proportional to the ion irradiation current. Specifically, if the ion beam current is increased, the ion beam machining time can be shortened. However, if the ion beam diameter is determined, the maximum value of the ion beam current will be determined by the performance of the ion source or the ion optical system. The ion current and beam diameter are determined by lens control values and aperture size. If the aperture size is increased the current increases, but as the lens aberration increases, the beam diameter also increases.

FIG. 2 schematically shows the machining procedure employed when forming a cross-section by a prior ion beam using three beam modes which focus on the ion beam current. Three beam modes A, B, and C are distinguished by the beam diameter and current. In mode A, the beam diameter is about 1 μm and the current is about 10 nA, in mode B the beam diameter is about 30 nm and the current is about 3 nA, and in mode C, the beam diameter is about 200 nm and the current is about 200 pA. First, the beam is scanned over a rectangle using the ion beam in mode A to form a rectangular hole. However, although the current is large, since the beam diameter is also large, the machined surface is a gently-sloping curved surface which is not suitable for observation. Therefore, next, the cross-section part is scanned by the ion beam in mode B to machine the cross-section more steeply. Finally, the cross-section to be observed is machined using the ion beam in mode C. In FIG. 2, it is seen that an electrode cross-section and a plug cross-section are exposed in an observed cross-section. In the case of a membrane for TEM observation also, the cross-section is similarly machined from both sides. Here, the ion beam in mode B or mode C has a small current, so a long time which is inversely proportional to the current is required, the time to observation was long, and observation of the cross-section cannot be realized in a short time.

To avoid polluting a silicon wafer with gallium and to return the silicon wafer after observing a cross-section to the process line, ions of non-polluting ionic species such as inert gas and oxygen are used. In this case, the ion source is changed to a liquid metal ion source or a plasma ion source, but the ion source luminosity falls by at least an order of 2 or 3. At this time, if a beam diameter of 0.1 μm is used to finish the cross-section, the current which can be obtained is several pA at most, so 1 hour or more is required to machine the cross-section. Therefore, perpendicular cross-sections of specific parts of the device could not be observed by non-contaminating ionic species.

It is therefore an object of the present application, which was conceived in view of the aforesaid problem, to improve the yield of a semiconductor device or the like by providing a machining method which can improve the machining precision of forming a cross-section by an ion beam without lengthening the machining time, by providing a machining method which shortens the time to separate or prepare separation of a micro sample without splitting a wafer, and by providing an ion beam system. It is a further object to provide a machining method which shortens the cross-section forming time, to provide a machining method which shortens the time to separate or prepare separation of an analysis sample from a wafer, and to provide an ion beam system when an inert gas, oxygen or nitrogen ions are used for the ion beam.

In the accordance with present invention, in order to improve machining precision while maintaining the machining time, the beam cross-section of the ion beam is formed in an elliptical shape. By forming it in an elliptical shape, an ion beam having respectively two different diameters in the minor axis and major axis direction of the ellipse can be generated. To machine a sample cross-section, the minor axis direction of a beam spot with a small diameter is used. Thereby, the sample machining precision can be improved as compared with the case where a circular beam is used.

When a sample is machined, the relative position of the ion beam and sample is controlled so that the minor axis direction of a beam with a small beam diameter is oriented toward the machining surface of the sample to be processed. The specific means for controlling the relative position will be described later in the embodiment.

The problem can be resolved by other means besides forming the ion beam spot in an elliptical shape. For example, the beam shape on the sample may be formed rectangularly using a frame like a stencil mask. In this case, the ion beam is formed so that, among the four sides of the rectangle, the steepness of at least one side is smaller than the steepness of the other three sides.

"Steepness" is a concept which indicates the gradient with which the beam intensity of the ion beam falls from its maximum to zero, and is quantitatively expressed by the skirt width of the ion beam profile. The means used to control steepness and the ion beam profile will be described later in the embodiment.

As described above, in accordance with the present invention, this problem is resolved by forming the ion beam so that the beam on the sample is asymmetrical with respect to the ion beam irradiation axis (ion beam optical axis) (this includes "non-axial symmetry" and asymmetry with respect to 90° rotation around the irradiation axis).

According to the present application, therefore, there is provided a machining method which can improve the machining precision of forming a cross-section by an ion beam without lengthening the machining time, a machining method which shortens the time to separate or prepare separation of a micro sample without splitting a wafer and an ion beam system. Further provided are a machining method which shortens the cross-section forming time, a machining method which shortens the time to separate or prepare separation of an analysis sample from a wafer and an ion beam system, when an inert gas, oxygen or nitrogen ions are used for the ion beam. Also provided is a novel inspection/analysis method which does not require wafers to be discarded due to testing, and does not generate defects even if wafers from which samples were removed for inspection are returned to the process. By using the electronic component manufacturing method according to the present application, wafers can be tested without splitting the wafer, new defects are not created and expensive wafers are not rendered useless. As a result, the manufacturing yield of electronic component production improves. Finally, there is provided an ion beam system which can implement the method of separating or preparing separation of analysis samples, the inspection/analysis method, and the electronic component manufacturing method.

BRIEF DESCRIPTION OF THE DRAWINGS

FIG. 5A is a diagram of a display screen of a central processing unit;

FIG. 5B is a diagram of a display screen of a central processing unit;

FIG. 5C is a diagram of a display screen of a central processing unit;

FIG. 9 is a diagram showing an argon ion beam intensity profile in the second embodiment;

FIG. 10 is a diagram which shows the rotation of a stencil mask;

FIGS. 15A to 15C show cross-sectional views from the side of a machined cross-section of a sample machined by the ion beam machining system of the fourth embodiment;

DETAILED DESCRIPTION OF THE PREFERRED EMBODIMENTS

First Embodiment

Figure 1:
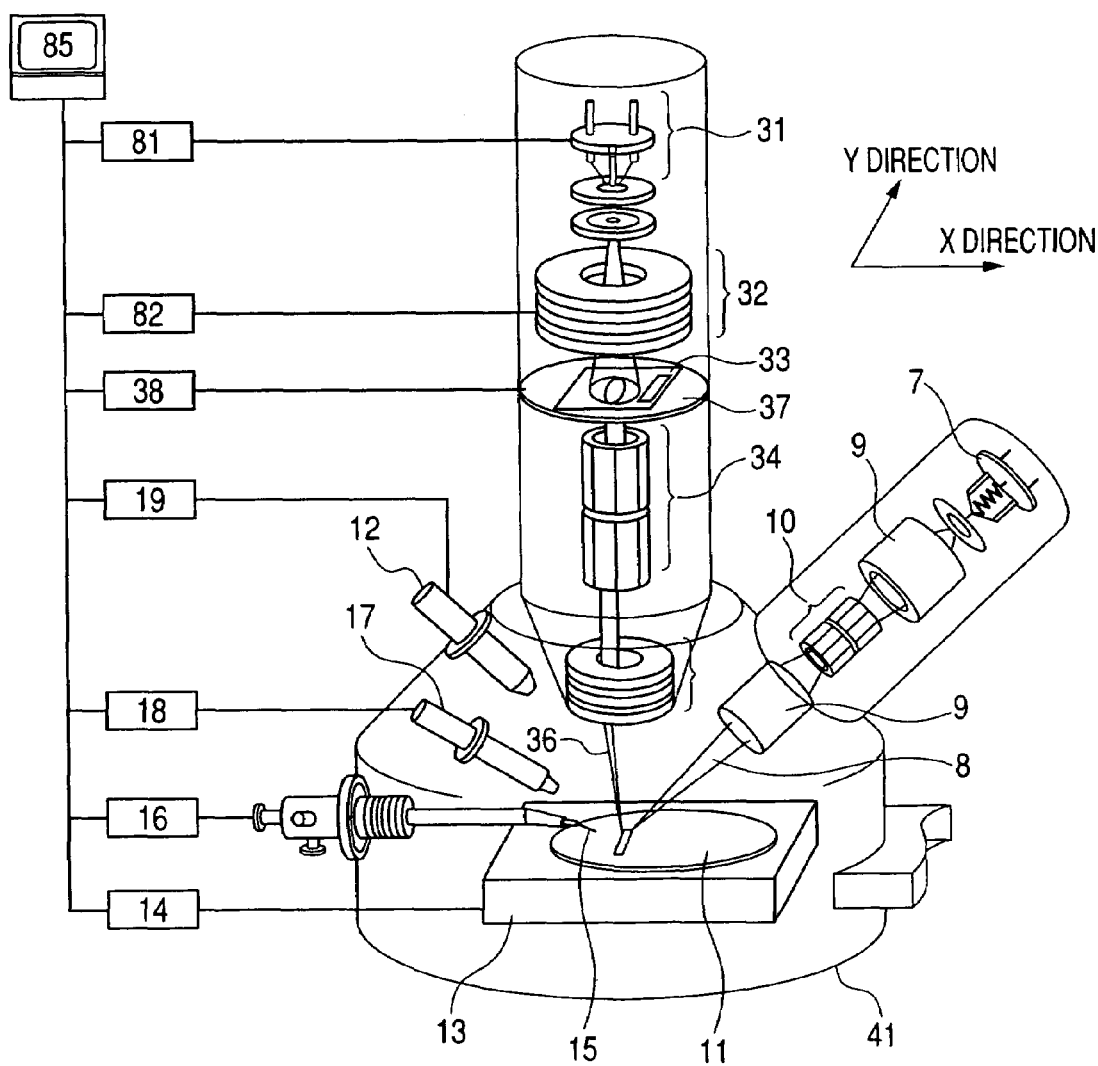
FIG. 1 is a diagram showing an ion beam machining system according to one embodiment of the present application.
Figure 2:
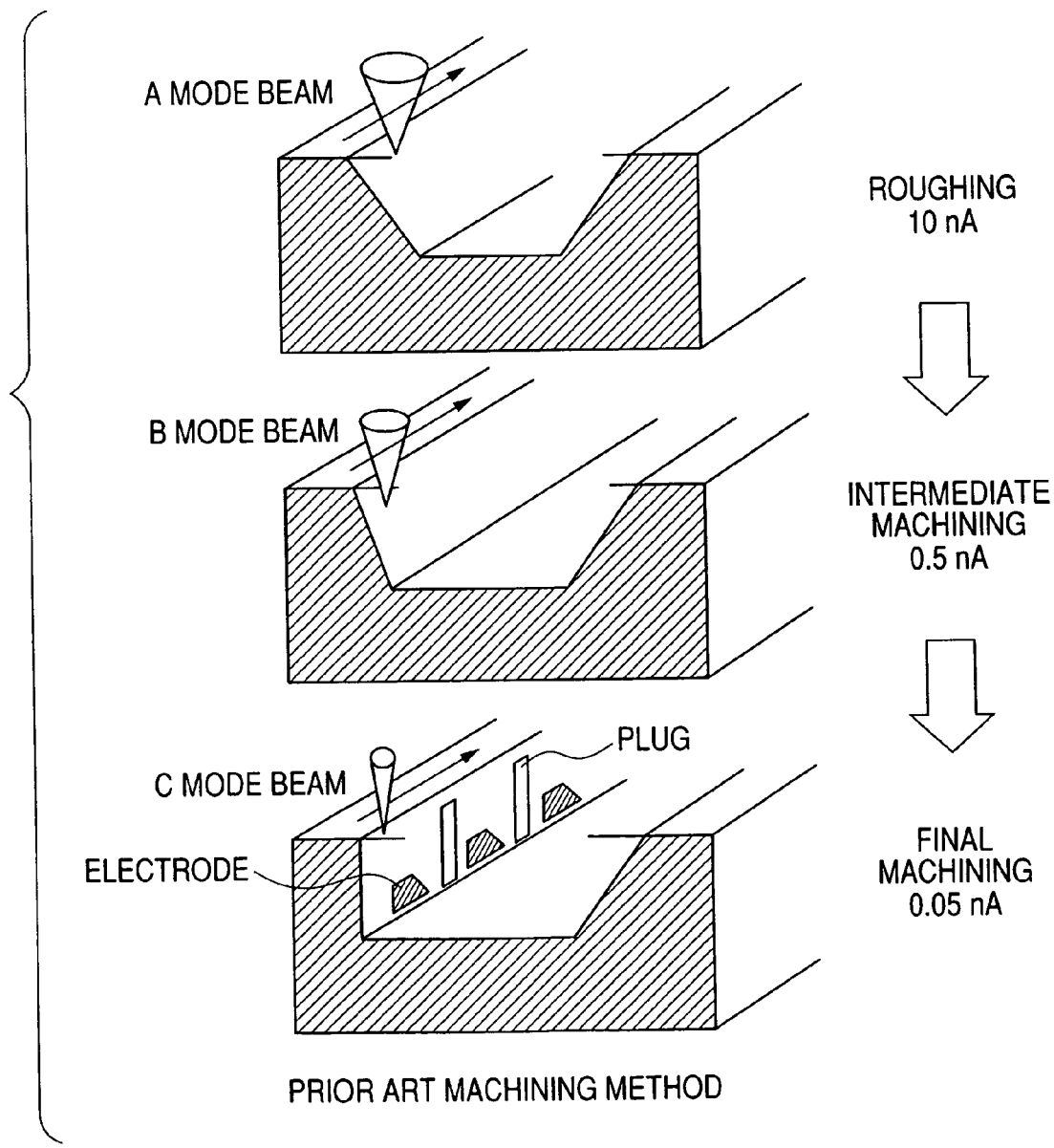
FIG. 2 is a schematic view showing the essential features of prior known ion beam machining.

In this embodiment, an example will be described wherein the shape of the ion beam spot is formed by an aperture having an elliptical or rectangular opening. FIG. 1 is a schematic view of an ion beam system according to this embodiment. This ion beam system 23 comprises a vacuum chamber 41, this vacuum chamber containing an ion beam irradiation system comprising a liquid metal ion source 31 which emits gallium ions, condenser lens 32, beam limiting aperture 33, aperture rotating mechanism 37, ion beam scanning deflector 34 and objective lens 35. An electron beam irradiation system comprising an electron source 7, electron lens 9 which converges the electron beam 8 emitted from the electron source 7 and electron beam scanning deflector 10 are also provided therein. Further provided are a secondary particle detector 12, sample stage 13, probe 14, precursor gas dispenser 17 and sample 11. This system is controlled by an ion source controller 81, lens controller 82, sample stage controller 14, manipulator controller 16, precursor gas dispenser controller 18, controller 19 of a secondary particle detector, aperture rotation controller 38, ion beam scanning controller 83 and central processing unit 85. Here, the central processing unit 85 is provided with a display which displays a data input means for a system user to input required data, the image generated based on the detection signal of the secondary particle detector and the data inputted by the data input means. The sample stage comprises a linear transposition mechanism which transposes it directly in two directions in the sample mounting plane, a linear transposition mechanism which transposes it in a direction perpendicular to the sample plane, a mechanism which rotates it in the sample mounting plane, and an inclination mechanism having an inclination axis in the sample mounting plane, these controls being performed by the sample stage controller 14 by a command from the central processing unit 85.

With this system, gallium ions emitted from the liquid metal ion source 31 are converged on the sample by the condenser lens and objective lens. The convergence condition setup is input to the central processing unit 85. The beam diameter irradiated on the sample is determined by imaging on the sample using the ion source as a light source and by the lens aberration. The lens aberration increases as the opening of the beam limiting aperture becomes larger, and the beam diameter increases.

Figure 3:
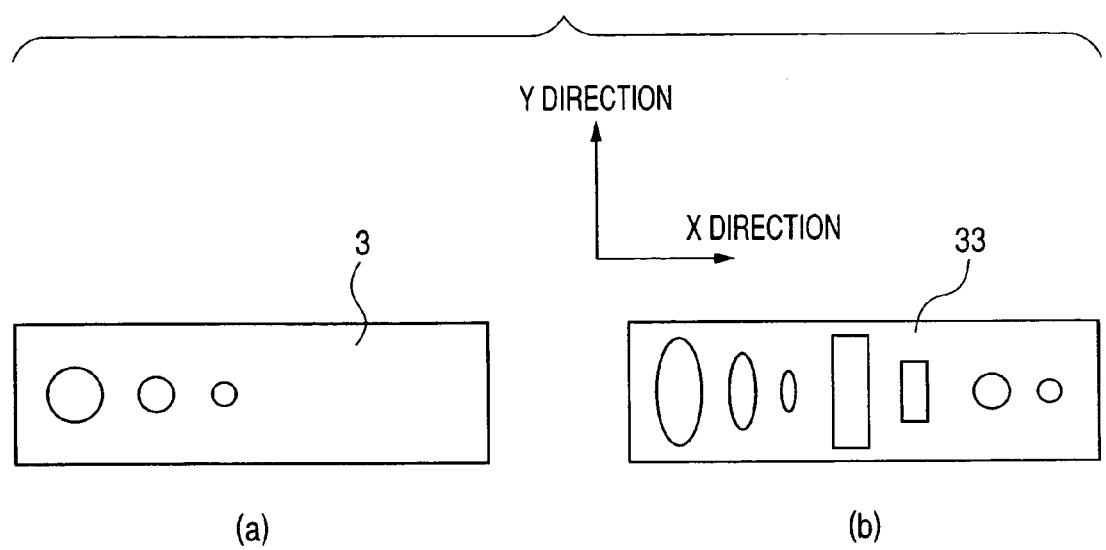
FIG. 3 is a comparative diagram showing a plan view of an axially symmetric beam limiting aperture, and a non-axially symmetric beam limiting aperture.

In FIG. 3, (a) and (b) represent examples of the plane shape of the beam limiting aperture. In FIG. 3, (a) shows an example of plural circular holes of different diameter with a prior art aperture 3. In FIG. 3, (b) shows an example of plural holes of non-axial symmetry, such as circular holes, elliptical holes and rectangular holes. The circular shape is the same as in the prior art, and is mainly used for image observation. The elliptical and rectangular shapes are used for forming cross-sections, and the direction of the major axis of the ellipse or the direction of the long side of the rectangle, i.e., the Y direction of FIG. 3, is the direction parallel to the cross-section. Further, when a beam is scanned over a rectangle, the direction of one side is made parallel to the Y direction. If the ion beam current density is almost uniform in the opening of the beam limiting aperture, and the ion beam current which reaches the sample is effectively proportional to the surface area of the opening. In this embodiment, although an ellipse or rectangle was taken as the beam limiting aperture, any shape with non-axial symmetry such that the width in a direction approximately perpendicular to the maximum width direction of the hole is effectively the minimum width may be used, and in the present application, this shape is referred to as elliptical or rectangular. Although it need not be mentioned, ellipse means a shape which does not have clear corners, and rectangle means a shape which has plural corners. The rectangular shape may not necessarily have four corners, and may have five or more, or three.

Figure 4:
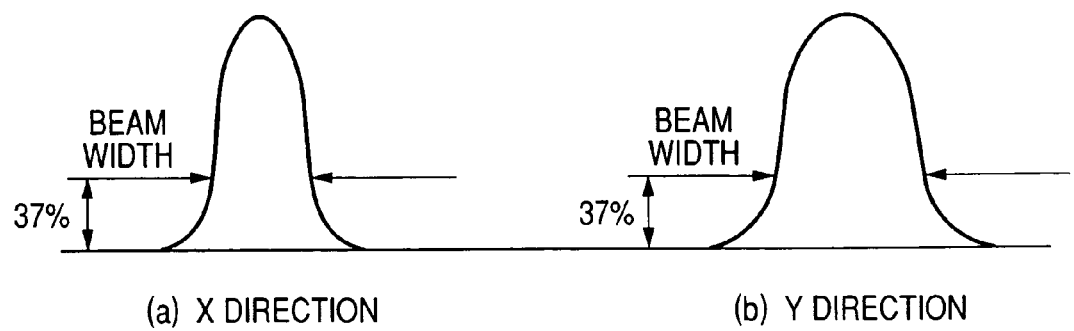
FIG. 4 is a diagram showing an ion beam intensity profile in a short axis direction and a long axis direction.

FIG. 4 shows the intensity profile obtained by passing the ion beam through the aperture having a non-axially symmetric opening (b) shown in FIG. 3. In FIG. 4, (a) is a profile cross-section of the beam projected on the sample when viewed from the X direction, and in FIG. 4, (b) is a profile cross-section of the beam projected on the sample when viewed from the Y direction. It is seen that the profile is finer in the X direction, broader in the Y direction and is formed with non-axial symmetry. If for example the length of the major axis is made twice that of the minor axis, since the surface area of the opening will be double that of a circle having the minor axis as diameter, the ion beam current will be approximately doubled. The beam diameter in the major axis direction will then be larger than in the minor axis direction, but its magnitude depends on the magnitude of the aberration.

In cross-section machining, the ion beam passing through the circular hole is first made to scan the sample by an ion beam scanning deflector 34. The secondary particle detector 12 then detects the secondary particles emitted from the sample. The intensity of the detection signal of the secondary particle detector 12 is modulated, and an image of the sample is displayed on the screen of the display of the central processing unit 85.

FIG. 5A shows a typical display 401 of the central processing unit 85. With this sample, a plug 501 is observed from the direction of an arrow 503 at the position of a broken line 502. However, on this screen, it is seen that the broken line is inclined at an angle θ to the Y direction. While the operator observes the screen, the sample stage is rotated until the broken line is parallel to the Y direction. By inputting position data concerning the broken line in FIG. 5A, the rotation angle can be calculated by the central processing unit, and the sample stage can also be rotated automatically. The position data concerning the broken line may for example be the position coordinate of the end point of the broken line. A system user inputs the position coordinate of the broken line to the central processing unit by for example specifying the end point of the broken line with a pointer.

FIG. 5B shows the screen after rotation. When the sample image is displayed on this screen, the rectangular area to be processed is set. For this setting, the operator may use a pointer on the screen, or input numbers from a keyboard. A sample image display area 403 is located in a scanning area setting window 402, and the sample image is displayed here. A beam scanning area 404 is set therein. For example, the positions [1]-[4] of the four corners of this rectangular area are specified using a pointer 405 on the screen, or coordinate numbers are inputted into a coordinate input display area 406.

Next, cross-section machining is performed by scanning the rectangular area using the ion beam which has passed through the elliptical hole whereof the length of the major axis is twice that of the minor axis. When cross-section machining is performed using this beam, since the ion beam current is twice that of the prior art circular beam, the machining time can be reduced to approximately ½ that of the prior known machining. In other words, by controlling the ratio of the major axis and minor axis, the ion beam current value can be controlled to an arbitrary magnitude for the case when the ion beam spot is formed in an axially symmetrical shape such as a circle having the length of the minor axis as a diameter. Hence, since the ion beam is not restricted in the major axis direction, the ion beam current increases, and since machining of the sample is performed in the direction of the minor axis of the beam spot, machining precision does not fall.

Here, it is important to set the system to have the non-axial symmetry characteristic and the cross-section forming direction described above. This setup can be fixed when the system is designed, but an aperture rotating mechanism may also be provided and a command issued from the central processing unit. Specifically, when setup is performed so that the direction of the major axis of the ellipse of the beam limiting aperture 33, i.e., the Y direction of FIG. 3, is parallel to the cross-sectional surface and the ion beam is made to scan the rectangular area on the sample by the ion beam scanning deflector 34, it is important to adjust the setting by the central processing unit so that the direction of one side of the rectangular area is parallel to the Y direction.

Likewise, if the beam scanning direction is made to coincide with the direction parallel to the cross-section, efficient cross-section machining can be performed. If the aperture rotating mechanism 37 which rotates the aperture around the ion beam irradiation axial center is provided, the direction of the minor axis of the ion beam can be set as desired. It is seen that the broken line on the display 401 of FIG. 5A is inclined at an angle θ to the Y direction. Hence, the operator may observe the screen, calculate the angle θ, and operate the aperture rotating mechanism to rotate the aperture by the angle θ so that the major axis direction of the aperture is parallel to the broken line (FIG. 5C). The rotation angle can also be calculated by the central processing unit by inputting position data concerning the broken line in FIG. 5A, and the aperture rotating mechanism operated based on rotation angle data from the central processing unit so that the aperture is rotated automatically.

Next, the procedure for observing the cross-section will be described. The electron beam 8 emitted by the electron gun 7 is converged, and irradiates the sample 11. When the sample cross-section is irradiated while scanning with the electron beam 8, the secondary particle detector 12 detects the secondary electrons emitted from the sample cross-section, and if the intensity is converted into an image luminosity, the sample cross-section can be observed. Specifically, if a rectangular hole is formed by FIB6 in an abnormal spot such as a defect or foreign matter in a circuit pattern, a cross-section of the defect or foreign matter can be observed by the electron beam 8, and the reason for its occurrence can be analyzed.

In TEM sample manufacture, if identical machining is performed from both sides of the surface to be observed, the same effect can be obtained, but in this case also it is necessary to control the non-axial symmetry and the cross-section forming direction of the aperture as described hereinabove.

The machining procedure for micro sample production of TEM samples will now be described with reference to FIG. 6.

Figure 6:
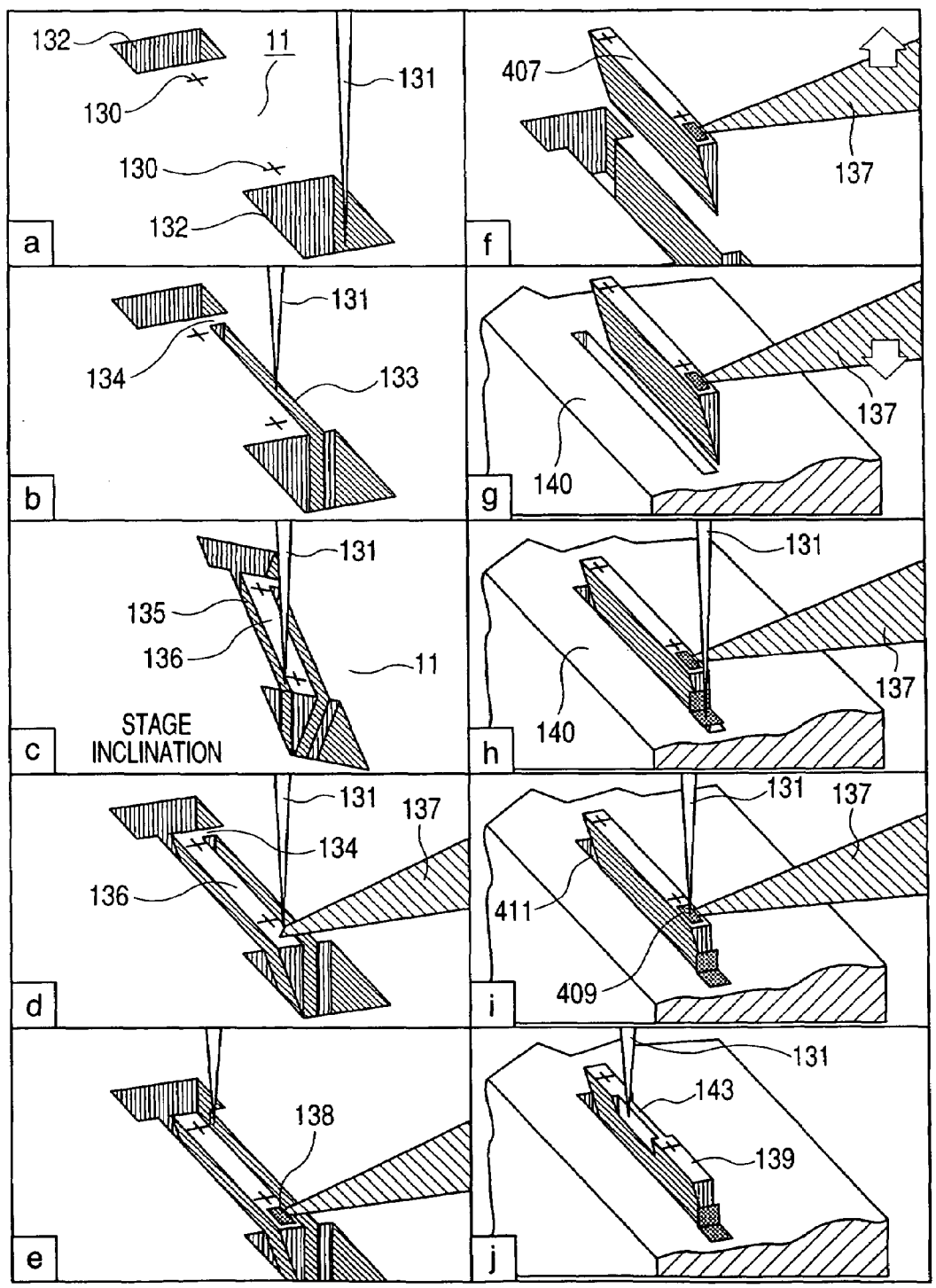
FIG. 6 is a diagram illustrating a flow for separating a micro sample from a sample.

In FIG. 6, at (a): First, two double-end marks 130 which form an observation cross-section are made using an ion beam current of approximately 100 pA. The line connecting these marks is equivalent to the broken line shown in FIG. 6 at (a). The observation positions are pinpointed by the marks while observing the image of the sample on the screen of the display of the central processing unit 85. In this case, a circular aperture is used, but here, the stage or aperture may be rotated beforehand so that the machining direction of the observation cross-section is aligned with the major axis direction of an elliptical aperture. Next, the aperture is changed to a larger circular hole and the current is increased to about 30 nA. Then, on the straight line which connects the two marks 130, two rectangular holes 132 are formed on either side of the marks 130.

In FIG. 6 at (b): Next, the aperture is changed over to an elliptical hole wherein the length of the major axis is twice that of the minor axis. The change-over operation may be performed when the system user inputs a change-over command via a data input means, or when the central processing unit transmits a change-over control signal to the aperture rotation controller 38. A current of about 10 nA is obtained. Under this condition, a long, thin perpendicular trench 133 is formed to intersect with one rectangular hole which does not intersect with the other rectangular hole. A small area which does not intersect with one of the rectangular holes 132 is a micro bridge 134 supporting the sample which is to be extracted later. Here, the long direction of the elliptical hole is parallel to the length direction of the trench. In this arrangement, although machining was performed by a current of about 5 nA with a prior art circular aperture, machining can now be performed with about twice the current, so the machining time can be reduced to about ½. Further, since the beam diameter in the direction of the cross-section to be observed is the same, steep machining can be performed toward the observation cross-section.

In FIG. 6 at (c): After the steps of (a) and (b), the sample stage is inclined by the sample stage controller so that the sample surface is slightly inclined (in this embodiment, by 25°). Hence, a long, thin trench 135 is formed so that the aforesaid rectangular holes 132 are connected. The oblique trench 135 is formed by a FIB which impinges obliquely to the sample surface, and it intersects with the perpendicular trench 133 which was formed previously. The micro bridge 134 is left by the steps (a)-(c), and the orthogonal triangular wedge-shaped micro sample having an apex of 25°, including the marks 130, is held in a cantilever state.

In FIG. 6 at (d): Next, the sample stage controller is operated, and the sample stage is returned to the horizontal. Here, the probe is driven by a probe controller, and a probe 137 at the tip of a transport means is brought in contact with the end of the sample 136 to be extracted which is opposite to the micro bridge 134. Next, a change-over is made to a circular aperture and the current is adjusted to about 200 pA. A change-over operation is also performed when the system user inputs a change-over command via the data input means or the central processing unit transmits a change-over control signal to the aperture rotation controller 38. To fix the probe 137 to the sample 136 to be extracted, a FIB 131 is then used to scan the sample while passing a precursor gas into an area including the tip of the probe 137. A deposition layer 138 is thereby formed in the FIB irradiation area, and the probe 137 and sample 136 to be extracted are connected.

In FIG. 6 at (e), (f): To extract a micro sample from the sample substrate, it is released from the support state by performing FIB irradiation and sputtering of the micro bridge 134.

In FIG. 6 at (g), (h): A micro sample 139 which is connected to the tip of the probe 137 is moved to the sample holder, and FIB irradiation is performed on the micro sample 139, sample holder 140 and contact part while introducing a precursor gas. Due to this operation, the micro sample can be connected to the sample holder 140.

In FIG. 6 at (i): Next, the probe 137 is separated from the micro sample 139 by irradiating the deposition layer 138 which connects the probe 137 with the micro sample 139 to perform sputter removal.

In FIG. 6 at (j): Finally, membrane machining is performed using elliptical apertures with 3 diameters. A thin finish is given to produce a wall 143 with an observation area having a thickness of about 100 nm or less using a small diameter hole in the order roughing, intermediate machining and finishing to give a TEM sample. As a result of the aforesaid machining, a TEM observation area is produced. Here, when the beam shape is elliptical, the machined shape is unsymmetrical. If this is done, membrane machining can be performed at about twice the speed as in the prior art. Here, an example was described where the operator controls the system using the input unit of the central processing unit, but it is also possible to provide a memory means such as a memory in the central processing unit, and store the control conditions of all the steps as a control sequence so that sampling is fully automated.

Figure 7A:
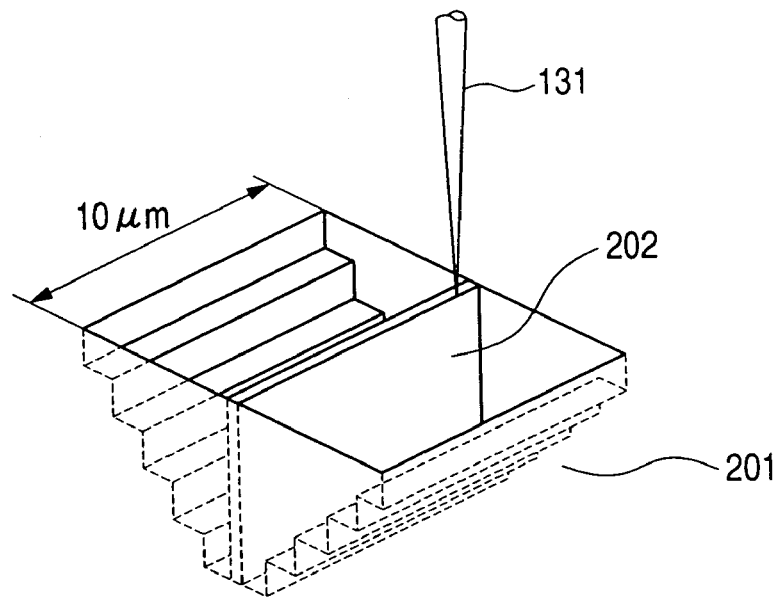
FIGS. 7A and 7B are diagrams showing a method of sample separation by electrostatic deposition.
Figure 7B:
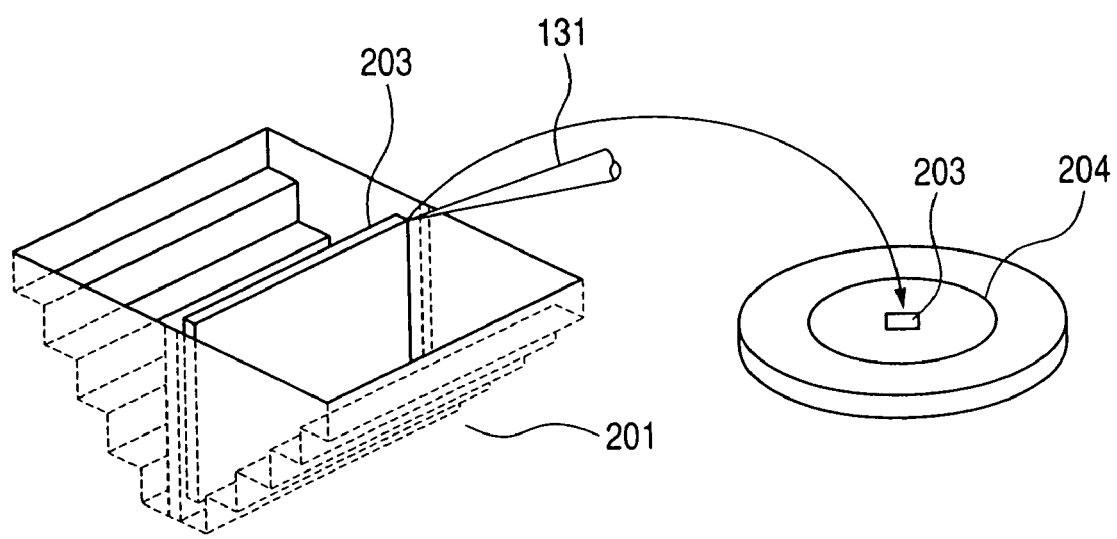

In the example shown in FIG. 6, the sample piece was extracted from the sample substrate using a probe, but the sample piece can also be extracted by electrostatic adsorption. FIGS. 7A and 7B show an example of extraction of the sample piece by electrostatic adsorption. FIG. 7A shows a case where both sides of a target position which forms the extraction sample are processed by the FIB 131 in stepwise fashion on a membrane 202 formed on a wafer 201. A sample membrane 203 is produced, FIG. 7B showing a case where the circumference around the sample membrane 203 is cut out by the FIB 131 leaving one part. The wafer 201 is removed from the ion beam system, the sample membrane 203 is completely separated from the wafer 201 in the atmosphere using the static electric charge of a glass stick, and is then moved to a TEM sample holder 204. By this method also, the separated sample membrane can be analyzed by TEM.

The peeling off of the sample piece by electrostatic adsorption may be performed inside a vacuum chamber. In this case, the sample manufacturing device shown in FIG. 1 is provided with a means for extracting a piece of micro sample made from a material which is easily charged with static electricity, such as a glass stick or a probe made of an insulating material. Specifically, provided that an ion beam with non-axial symmetry is used, the system and method used to machine the micro sample for observation/analysis are within the scope of this embodiment of the invention.

After performing wall machining as described above, the micro sample is introduced into the TEM sample chamber. In TEM observation, cross-sections of defects and foreign matter can be observed with higher resolution than in SEM observation, and the cause of defects can be analyzed in more detail from the observation results. The ion beam system of this embodiment of the invention includes not only a FIB-SEM device which combines the ion beam case described above with an electron beam case, but also a device wherein cross-section machining is performed by an ion beam system having only an ion beam case, and the sample is transported to an electron microscope for observation.

According to above embodiment of the invention, to improve the yield of a semiconductor device or the like, there is therefore provided a machining method which shortens the machining time required to form cross-sections by an ion beam, a machining method which separates the micro sample without splitting the wafer, and an ion beam machining system.

Second Embodiment

In this embodiment of the invention, an ion beam system which forms a beam shape on a sample with a stencil mask, and makes the beam profile unsymmetrical with respect to two perpendicular directions, is described. Specifically, in this embodiment, the case is described wherein a stencil mask with an opening of specified shape is inserted midway in the ion beam irradiation system, and the formed beam wherein the opening shape is projected on the sample, is used. By enlarging the opening area of the stencil mask even under conditions which make the skirt shape of the beam profile about the same as that of the focused ion beam described in the aforesaid first embodiment, such a formed beam can increase the ion beam current.

Figure 8:
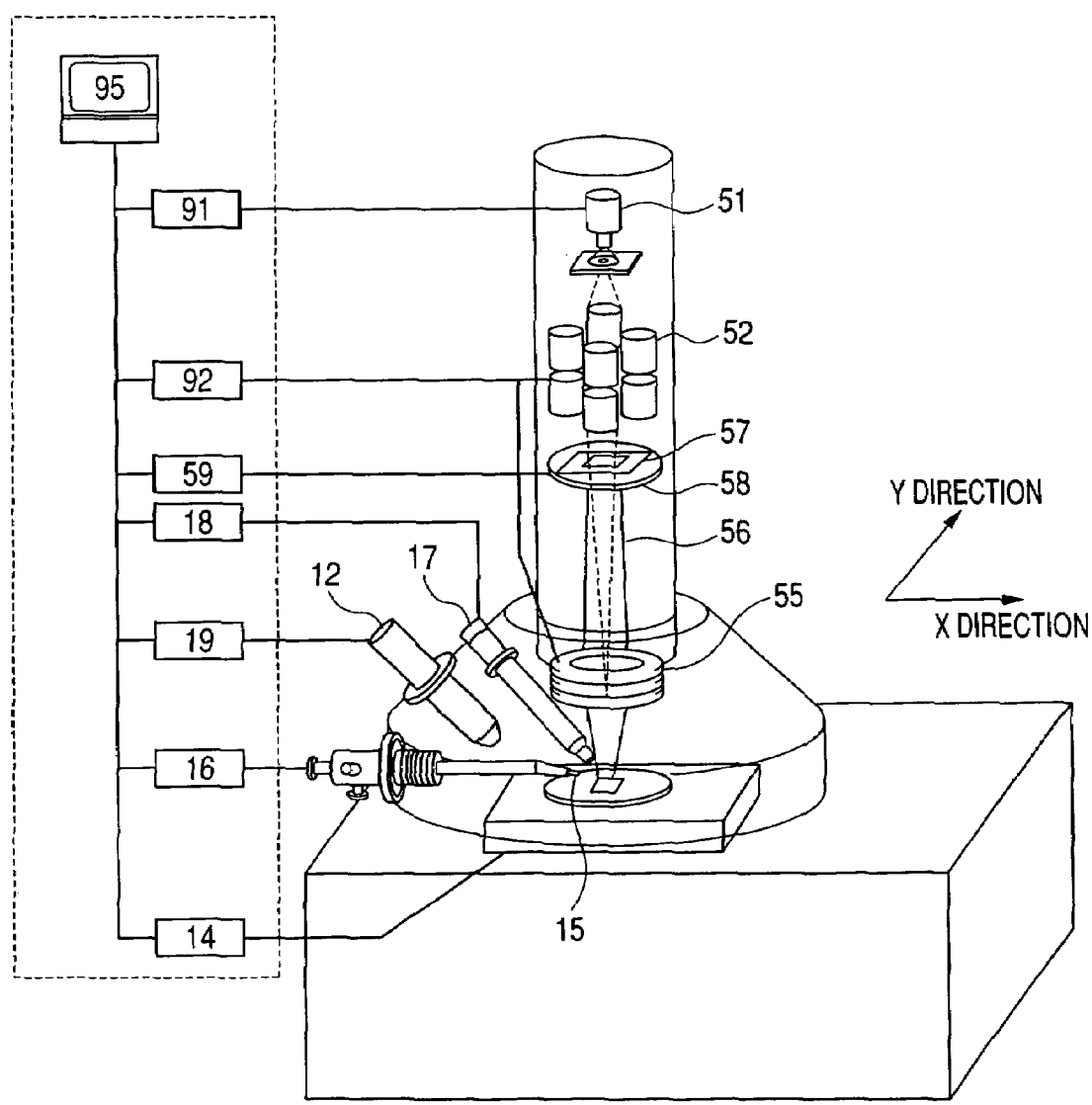
FIG. 8 is a diagram showing the overall appearance of an ion beam machining system according to a second embodiment.

FIG. 8 shows a schematic view of the ion beam system of this embodiment. This ion beam system comprises a vacuum chamber 41, this vacuum chamber having an ion beam irradiation system comprising a duoplasmatron 51 which emits gaseous ions such as argon, neon, xenon, krypton, oxygen and nitrogen, a non-axially symmetric ion beam lens 52, objective lens 55, stencil mask 57 and stencil mask rotating mechanism 58. Also disposed therein are a secondary particle detector 12, sample stage 13, probe 15, precursor gas dispenser 17 and sample 11. The device which controls this system comprises a duoplasmatron controller 91, lens controller 92, sample stage controller 14, manipulator controller 16, precursor gas dispenser controller 18, secondary particle detector controller 19, stencil mask rotation controller 59 and central processing unit 95. Here, the central processing unit 95 is provided with a display which displays an image generated based on the detection signal of the secondary particle detector, or the data inputted by a data input means. The sample stage comprises a linear transposition mechanism which transposes the sample directly in two directions in the plane of the sample mounting device, a linear transposition mechanism which transposes the sample in a direction perpendicular to the plane of the sample mounting device, a rotating mechanism in the plane of the sample mounting device and an inclination mechanism having an inclination axis in the plane of the sample mounting device, these controls being performed by a sample stage controller 14 on a command from the central processing unit 95.

Here, by opening a gas valve midway in the piping from an argon cylinder, argon gas is introduced into the duoplasmatron 51 and a plasma is generated by a gas discharge. An ion beam 58 is then extracted from the duoplasmatron 51. These operations are performed by the duoplasmatron controller on a command from the central processing unit. This ion beam 58 is converged near the center of the objective lens 55 by the non-axially symmetric ion beam lens 52 which is a double quadrupole lens. The voltage applied to the electrode of the non-axially symmetric ion beam lens 52 is set by the central processing unit 95 as a value calculated beforehand so that that this condition is satisfied. Here, the lens is designed so that the image surfaces of the double quadrupole lens coincide in the X and Y directions while the magnifications are different, and is set by the central processing unit 95 by a voltage value under the condition that both X and Y directions converge near the center of the objective lens 55. The ion beam 58 passes through the stencil mask 57 which has a rectangular hole. The objective lens 55 is controlled such that the stencil mask is projected on the sample 11. Here also, the voltage applied to the electrode of the objective lens 55 is set by the central processing unit 95 as a value calculated beforehand so that the aforesaid condition is satisfied. Then, a rectangular formed ion beam is irradiated on the sample.

Here, if the voltage is set so that the magnification in the X direction of the double quadrupole lens is small compared with the magnification in the Y direction, the ion beam which passes through the objective lens has a smaller divergence in the X direction compared with the Y direction, so the effect of aberration of the objective lens becomes small. The skirt shape of the beam profile in the X direction therefore becomes steep compared with the Y direction, the end face shape of the hole machined by the forming beam becomes steep in the X direction as compared with the Y direction, and the shape is then suitable for cross-section observation.

Referring to FIG. 9, the non-axial symmetry in the X, Y directions of the beam profile of the non-axially symmetrical beam will now be described. In order to quantitatively describe the steepness of the beam profile edge, in this embodiment, the skirt width of the beam profile is used as a measure of steepness. In this embodiment, as shown in FIG. 9, the skirt width of the beam profile was defined as the distance from 16% to 84% of the beam intensity. In the beam profile shown in FIG. 9, it is seen that the skirt width in the X direction is narrower than the skirt width in the Y direction, therefore in the rectangular beam shape shown in FIG. 9, the long side is steeper than the short side. To define the steepness of the edge part of the beam spot, a definition other than the width of the skirt may also be used.

Here, it is important to control the unsymmetrical symmetry of convergence by the ion lens and the cross-section forming direction as described above. Specifically, it is important that the voltage is set by the central processing unit 95 so that the magnification of the double quadrupole lens in the X direction is smaller than the magnification in the Y direction, and that as shown in FIG. 9, when the skirt shape of the beam profile is made steeper in the X direction than in the Y direction, it is set parallel to the cross-section which will form the Y direction. In particular, if the stencil mask position is adjusted so that the ion beam irradiation axis overlaps with the cross-section position, and the rectangular hole end side of the stencil mask 57 overlaps with the irradiation axis, the skirt width of the beam can be controlled smaller.

When an ion beam scanning deflection electrode is added to this ion beam system in an intermediate position between the stencil mask 57 and objective lens 55, and scanning is performed by the beam to produce a cross-section, if the beam scanning direction is made to coincide with the cross-section parallel direction, efficient cross-section machining can be performed. Specifically, as shown in FIG. 9, it is important that when the skirt shape of the beam profile is made steeper in the X direction than in the Y direction, the rectangular area scanned by the beam is set by the central processing unit 95 so that the direction of at least one side in the beam scanning direction is parallel to the Y direction.

Also, if a mechanism which limits the size of the mask hole in the stencil mask is provided, and the machining position is set by scanning the sample with the forming beam projected through this hole to acquire a sample image, a precise position setting can be performed. The mechanism which limits the size of the mask hole may for example be a structure which superimposes a fine aperture on the stencil mask.

In TEM sample manufacture, if the same machining is performed from both sides of the surface to be observed, an identical effect can be acquired, but in this case also, the unsymmetrical convergence by the ion lens and the cross-section forming direction must be controlled as described above.

The machining procedure for micro sample production can be made identical to that of the method shown in FIG. 6, but care must be taken that the final machined shape is unsymmetrical by making the beam shape rectangular and the skirt width of the beam unsymmetrical in the X direction and the Y direction. This can be done by system design.

Specifically, the design is such that in forming the thin, long trench 133 in step (b) of FIG. 6 and the thin, long trench 135 in step (b) of FIG. 6, the direction perpendicular to the thin, long trench 133 and the thin, long trench 135 is the direction in which the skirt width of the beam profile is smaller.

If the stencil mask rotating mechanism 58 which rotates the stencil mask around the ion beam irradiation axis is provided, the shape of the forming beam can be rotated in any direction, as shown in FIG. 10. For this purpose, if the voltage applied to the electrodes of the double quadrupole lens is set by the central processing unit 95 so that the skirt width of the profile is smaller towards the edge of the forming beam, a forming beam which can form a cross-section in any direction of the sample surface can be obtained. In other words, a cross-section in any direction of the sample structure can be observed, and cross-sections in many directions can be observed without driving the sample stage any further.

To control the skirt width of the beam in this embodiment, a double quadrupole lens was taken as an example of a non-axially symmetric ion beam lens, but as long as non-axial symmetry control is possible, another quadrupole lens, an 8 pole lens or a 16 pole lens may also be used. Combinations thereof, and combinations thereof with symmetrical lenses, may also be used. Also, in the above embodiment, an example was described where the forming beam projected the shape of a mask opening on the sample, but the spot shape of the ion beam may be formed by an aperture having an elliptical or rectangular opening instead of the forming beam.

An unsymmetrical beam-forming technique as described in this embodiment can increase the ion beam current as compared with the case when control is performed so that the X and Y directions are both steep profiles, i.e., the case where the beam is formed symmetrically. Therefore, the beam forming technique of this embodiment is preferably an ion beam of gaseous elements such as argon or oxygen. In the first embodiment, an example was described where a Ga ion beam was converged, but Ga remains in the machining area. In the manufacture of semiconductor devices such as silicone devices, since Ga which is a heavy metal is very likely to cause defects when a sample piece is produced, it is desirable to use an ion beam of gaseous elements such as an inert gas, oxygen or nitrogen, which do not much affect the sample properties. However, with the ion sources presently available, using plasma ion sources which generate gaseous element ions, the luminosity of the ion beam which can be generated is lower by 2 or 3 orders of magnitude than with liquid metal ion sources such as Ga. Therefore, by deliberately forming the ion beam asymmetrically and performing the actual machining using the beam profile's steeper part, an ion source of low luminosity can be used without reducing the machining precision. This approach is effective not only with ion beams of gaseous elements (for example elements such as nitrogen, oxygen, neon, xenon and krypton, or mixed ion beams thereof), but when using any ion source of low luminosity.

Regarding the steepness of the skirt of the beam profile, by controlling the steepness ratio in two perpendicular directions compared to the case where the skirt of the beam profile is made symmetrical in the X direction and Y direction, the ion beam current value can be controlled to any desired magnitude. In other words, since there is a direction which is not so steep, the ion beam current increases, but as machining of the sample is performed in the steep direction of the beam profile, machining precision does not fall.

In this embodiment, to control the skirt width of the beam, an ion beam lens with non-axial symmetry was used, but a combination of an aperture which makes the ion optical source non-axially symmetric and a symmetrical ion beam lens may also be used. Specifically, the aperture through which ions from the ion source are emitted can be made elliptical or rectangular, or a similar non-axially symmetric aperture can be provided midway and the lens adjusted using this aperture as a light source. In this case also, the lens condition setup can be performed by the central processing unit.

To produce micro samples for an analysis means such as TEM and SEM, the forming beam of this embodiment can be used for the sample piece production flows shown in FIG. 6 or FIGS. 7A and 7B. The ion beam system of this application includes not only the ion beam system described in this embodiment, but also an ion beam system wherein cross-section machining is performed by an ion beam and cross-section observation is performed by an electron beam, which is a FIB-SEM device combining an ion beam case with an electron beam case.

According to the sample manufacturing method and sample manufacturing device described in this embodiment, in addition to the effect of the sample manufacturing method and sample manufacturing device described in the first embodiment, high-precision machining can be performed with a larger current by using a stencil mask. The beam current can be increased and machining precision can be increased even with an ion source of low luminosity, and cross-section machining and micro sample production can be performed in a short time. This means that ion beams of gaseous elements such as inert gases, oxygen and nitrogen which have little effect on sample properties can be used instead of Ga which is very likely to cause defects. To increase semiconductor device yield, cross-sections can be formed by an ion beam without contaminating wafers with metals such as Ga, and micro samples can be separated or separation prepared without splitting wafers. Hence, according to this new inspection/analysis method, wafers do not have to be discarded for evaluation, and wafers from which samples have been removed for inspection can be returned to the process without causing defects. Wafers can also be evaluated without splitting, there are no new defects and expensive wafers are not rendered useless. As a result, semiconductor device manufacturing yield is improved.

Third Embodiment

In this embodiment, an example will be described wherein an ion source is disposed at an inclination to a FIB column, and the ion beam shape is formed using a stencil mask. Here, assume that the ion source uses a plasma ion source from which an ion beam of gaseous elements, such as inert gases, oxygen and nitrogen, is extracted. If an element such as an inert gas, oxygen or nitrogen is selected as the ion species of the ion source, since the electrical properties of the device are not affected, there are few defects even if processed wafers after ion beam machining are returned to the process. However, in such an in-line application, there was still the problem that defects occasionally occurred when metallic impurities were generated in minute amounts in the plasma ion source, and reached the sample. One of these impurities is metal ions, and another is metal neutral particles. Neutral particles cannot be controlled by the lens or an electrostatic deflection device, and the sample is extensively irradiated by them. There was also the problem that, when the sample was irradiated by neutral particles of gaseous ions, parts other than desired parts were also machined, and the sample deteriorated.

In this embodiment, an example is first described concerning a structure wherein the axis along which the ion beam from the ion source is extracted and the axis along which the ion beam irradiates the sample are inclined with respect to each other to avoid neutral particle impurities from reaching the sample. In general, the luminosity of the plasma ion source which can be generated is lower than that of a liquid metal ion source such as Ga by at least 2 or 3 orders of magnitude. Hence, in this embodiment, a stencil mask with an opening of predetermined shape is inserted midway in the ion beam irradiation system, and a forming beam which projects the opening shape with non-axial symmetry onto the sample is used.

Figure 11:
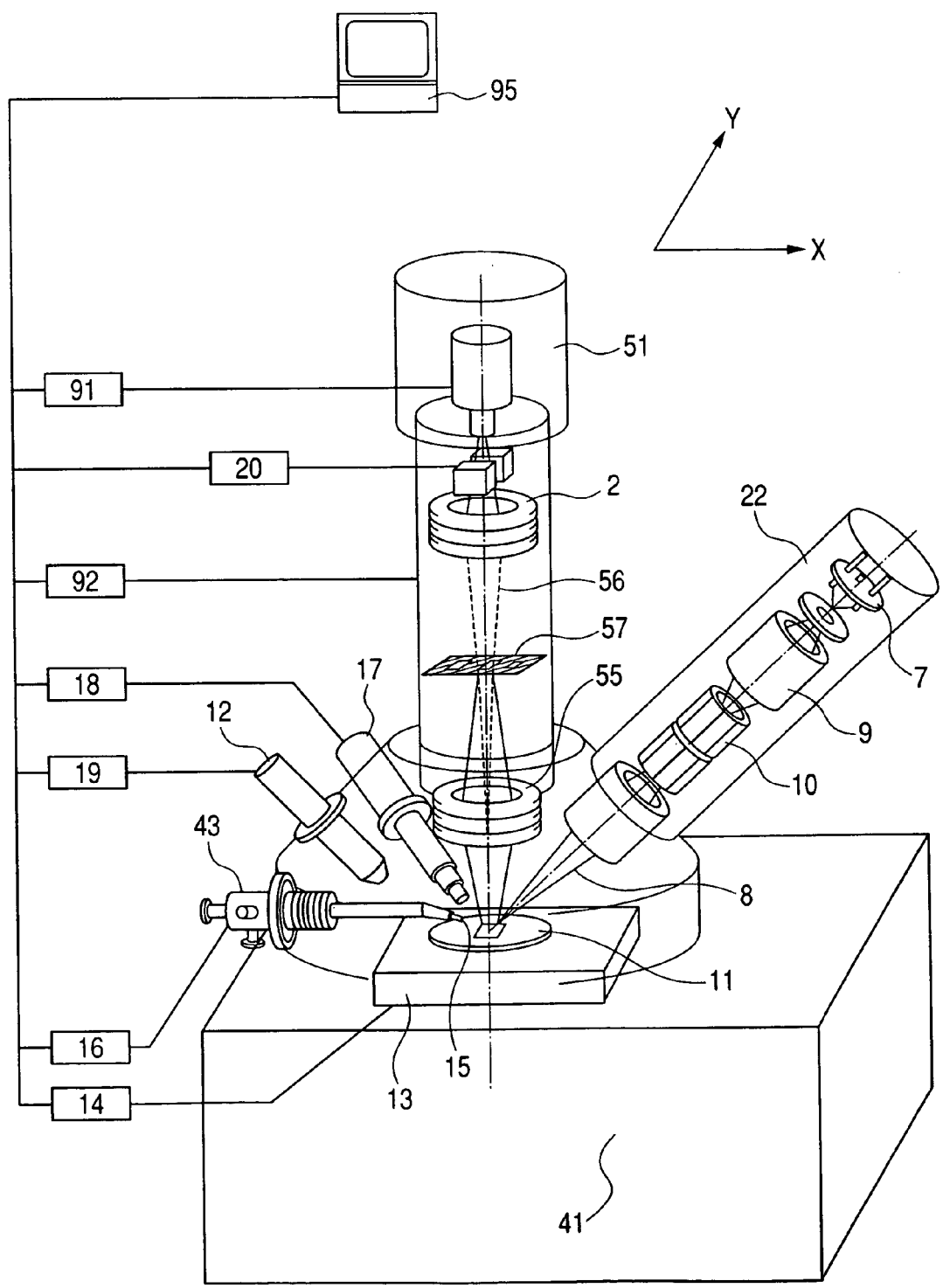
FIG. 11 is a diagram showing the overall appearance of an ion beam machining system according to a third embodiment.

FIG. 11 shows the ion beam system of this embodiment. The ion beam system comprises an ion beam irradiation system comprising a duoplasmatron 51 which emits gaseous ions such as argon, neon, xenon, krypton, oxygen and nitrogen, a condenser lens 2, an objective lens 55, a stencil mask 57, an ion beam deflector 60 and a FIB column tube 42 which houses these items. The system further comprises an electron beam irradiation system comprising an electron source 7, electron lens 9 which converges an electron beam 8 emitted from the electron source 7, electron beam scanning electrode 10 and electron beam column tube 22 housing these items.

A vacuum sample chamber 41 is disposed in the lower part of the FIB column tube 42 and SEM column 22, and a secondary particle detector 12, sample stage 13 on which a sample 11 is placed, probe 15, precursor gas dispenser 17 and manipulator 43 are housed in the vacuum sample chamber 41. The interior of the FIB column tube 42 is of course also maintained under vacuum. The system is controlled by a duoplasmatron controller 91, lens controller 92, sample stage controller 14, manipulator controller 16, precursor gas dispenser controller 18, secondary particle detector controller 19, ion beam deviation controller 20 and central processing unit 95. Here, the central processing unit 95 is provided with a display which displays an image generated based on the detection signal of the secondary particle detector or data inputted by the data input means. The sample stage is provided with a linear transposition mechanism which transposes it directly in two directions in the sample mounting plane, a linear transposition mechanism which transposes it in a direction perpendicular to the sample plane, a mechanism which rotates it in the sample mounting plane, and an inclination mechanism which has an inclination axis in the sample mounting plane, these controls being performed by the sample stage controller 14 by a command from the central processing unit 95. Although not clear from FIG. 11, the duoplasmatron 51 of this device is inclined with respect to the tube of the FIB column. Specifically, it is inclined in the Y direction of FIG. 11, and the direction in which the ion beam is extracted from the ion source and the irradiation axis of the ion beam are inclined to each other.

Next, the operation of this system will be described. First, by opening a gas valve midway in the piping from the argon cylinder, argon gas is introduced into the duoplasmatron 51 and a plasma is generated by a gas discharge. An ion beam 56 is then extracted from the duoplasmatron 51. Since the ion beam extraction axis and the sample irradiation axis are inclined to each other, the ion beam is refracted by the ion beam deflector 60. However, the neutral particles generated by the ion source are not deflected by the ion beam deflector 60, and continue straight on as they are. The operation of the duoplasmatron 51 and ion beam deflector 60 is controlled by the duoplasmatron controller 91, ion beam deflector controller 20 or central processing unit 95 upon a command from the central processing unit. This ion beam 56 is converged near the center of the objective lens 55 by the condenser lens 2. Specifically, the voltage applied to the electrode of the condenser lens 2 is set by the central processing unit 95 as a value calculated beforehand to satisfy this condition. The ion beam 58 passes through the stencil mask 57 which has a rectangular hole. The objective lens 55 is controlled so as to project the stencil mask on the sample 11. Here too, the voltage applied to the electrode of the objective lens 55 is set by the central processing unit 95 as a value calculated beforehand to satisfy this condition. Hence, a rectangular forming ion beam is irradiated on the sample. If this forming ion beam continues to be irradiated, a rectangular hole will be formed in the sample.

Next, the cross-section observation procedure will be described. The electron beam 8 emitted from the electron source 7 is converged to irradiate the sample 11. At this time, if a sample cross-section is irradiated while scanning with the electron beam 8, the secondary electrons emitted from the sample cross-section are detected by the secondary particle detector 12 and their intensity is changed into an image luminosity, the sample cross-section can be observed. If depressions (rectangular holes, etc.) are formed by the forming beam in abnormal parts such as defects or foreign matter of a circuit pattern, the wall surfaces of these depressions such as defects or foreign matter can be observed by the electron beam 8, and the reason for their occurrence can be analyzed.

Figure 12A:
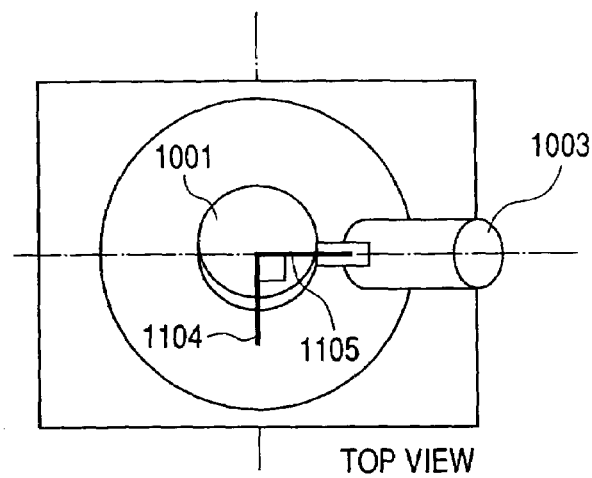
FIG. 12A shows a top view.
Figure 12B:
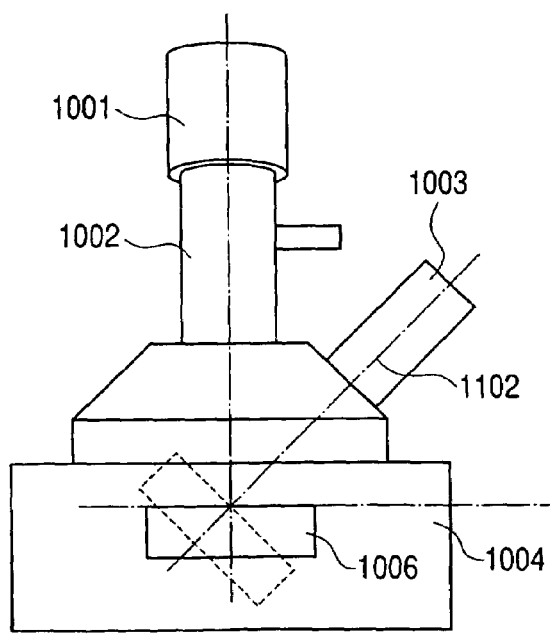
FIGS. 12B and 12C show a plan view and side view of the ion beam machining system of the third embodiment.
Figure 12C:
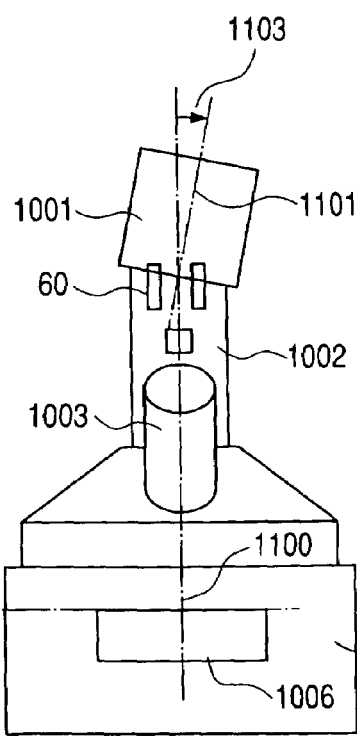

FIG. 12A is a top view, FIG. 12B is a front view and FIG. 12C is a side view of the device. In FIG. 12A, 1001 is a tube which houses the duoplasmatron, 1002 is a FIB column tube disposed in the lower part of the duoplasmatron and 1003 is a SEM column tube, and the broken dotted lines in the vertical and horizontal directions in the figure are central lines in the X direction and the Y direction of the sample stage. The intersection point of the broken dotted lines is the intersection point of the center axis of the FIB column tube and the sample mounting surface of the sample stage, and generally coincides with the center of the sample mounting surface. From the top view of FIG. 12A, it is seen that the duoplasmatron 1001 is inclined with respect to the FIB column 1002 (upper part of FIG. 12A). A segment 1104 is a line connecting the intersection of an extrapolation of the center axis of the duoplasmatron tube 1001 with the sample stage, and the intersection of the center axis of the SEM column tube with the sample stage, while a segment 1105 is a line which is a projection of the center axis of the SEM column tube on the sample stage. The feature of this invention is a construction wherein the axis 1101 along which the ion beam is extracted from the ion source and the axis 1100 along which the sample is irradiated can be inclined with respect to each other, and the aforesaid segment 1104 and segment 1105 can be made not parallel to each other but preferably arranged orthogonal to each other. To describe this more simply, the center axis of the FIB column tube and the center axis of the SEM column tube are in the same plane perpendicular to the sample mounting surface of the sample stage, the center axis of the duoplasmatron being inclined at a predetermined angle to the surface formed by the aforesaid FIB column center axis and SEM column center axis.

Referring now to FIG. 12B and FIG. 12C, the relation of the columns will be described in further detail. In FIG. 12B, the FIB column tube 1002 and the SEM column tube are arranged so that the center axes 1100 and 1003 of each intersect at the center of the sample mounting surface of the sample stage 1006. In the case of SEM observation, a primary electron beam is irradiated effectively parallel to the center axis 1102. Next, referring to FIG. 12C which is a side view, it is seen by comparing with FIG. 12A and FIG. 12B that the duoplasmatron 1001 is inclined with respect to the FIB column 1002. It is also seen that, since the center axis 1100 of the FIB column 1002 appears to pass through the center of the SEM column 1003, the SEM column 1003 and FIB column 1002 are disposed so that their center axes are in the same plane. The duoplasmatron 1001 is inclined with respect to the aforesaid plane. In a construction where the ion source is inclined with respect to the FIB column, neutral particles generated by the ion source are scattered in the ion emission direction, and since they are interrupted by a fixed aperture on the way, they do not reach the sample and contaminate the sample with neutral particle impurities, so the device manufacturing yield is not decreased. However, it was found that since the ion beam extracted from the ion source is refracted in the direction of the FIB column, the skirt width of the intensity profile of the projected beam expands, and became a hindrance to forming a steep cross-section. This is due to the fact that the energy of the ions, varies for each ion. When the ion beam is deflected by the ion beam deflector, a spread appears in the ion beam orbit in the deflection direction due to this energy difference. It was found that this effect extends also to a forming ion beam, and the skirt width is expanded in the direction in which the ion beam is refracted by the ion beam deflector, i.e., in the direction of the segment 1104 of FIG. 12A. Therefore, a steep machining edge is formed in the direction of the segment 1105, and a blunt machining edge is formed in the direction of the segment 1104 in the beam spot which actually irradiates the sample. Of course, the part formed with a steep edge has good machining precision and the machined cross-section is also good, so with this system, the SEM column was disposed so that SEM observation could be performed from a direction parallel to the direction of the segment 1105. However, the direction of the SEM column is not necessarily parallel to the direction of the segment 1105, and provided that it is disposed so as to avoid the direction parallel to the segment 1104, SEM observation in the direction of worst machining precision can be avoided.

Figure 13A:
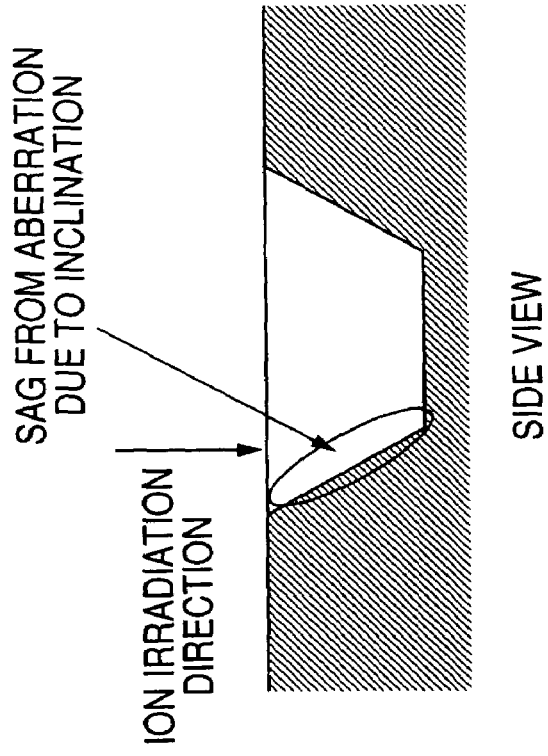
FIGS. 13A and 13B are cross-sectional views as seen from the side of a machined cross-section of a sample machined by the ion beam machining system of the third embodiment.
Figure 13B:
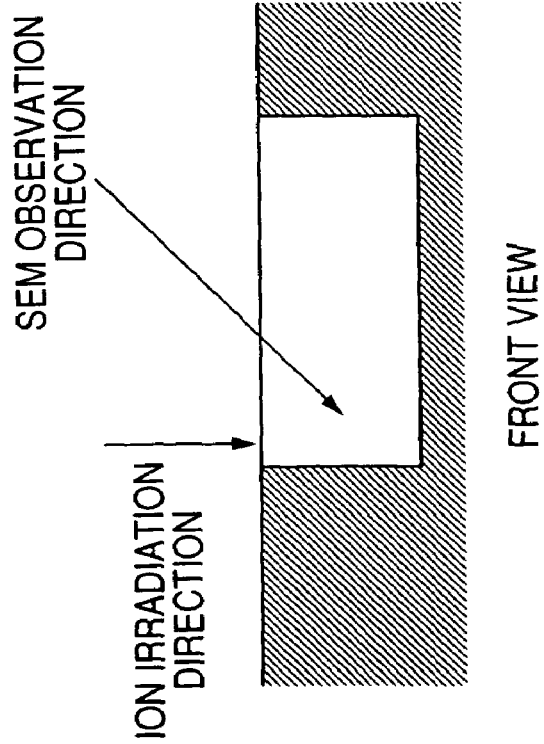

FIG. 13A is a cross-sectional view of the machined hole formed in the sample by FIB from the system as seen in FIG. 12B. In FIG. 13A, the direction shown by the arrow as "SEM observation direction" is the machined cross-section on the steep side of the beam spot, and a steep cross-section is formed. On the other hand, FIG. 13B is a cross-sectional view of the machined hole formed in the sample by FIB from the system as seen in FIG. 12C. In FIG. 13B, the part shown by a circle is a cross-section machined on the blunt side of the FIB beam spot, and an ill-defined cross-section is formed compared with the machined surface of FIG. 13A.

In this embodiment, an axially symmetric lens was used for the condenser lens, but it may be substituted by a non-axially symmetric lens which is a double quadrupole lens. In this case, the ion beam 56 is converged near the center of the objective lens 55 by the non-axially symmetric lens. Here, the lens is designed so that the image surfaces of the double quadrupole lens coincide in the X and Y directions while the magnifications are different, and is set by the central processing unit 95 to a voltage value such that both X and Y directions converge near the center of the objective lens 55. The ion beam 56 passes through the stencil mask 57 which has a rectangular hole. The objective lens 55 is likewise controlled so that the stencil mask is projected on the sample 11. The sample is then irradiated by a rectangular formed ion beam. Here, if the voltage is set so that the magnification in the X direction of the double quadrupole lens is small compared with the magnification in the Y direction, the ion beam which passes through the objective lens has a smaller divergence in the X direction than in the Y direction, so the effect of aberration of the objective lens becomes small. At this time, the skirt shape of the beam profile is steeper in the X direction than in the Y direction as shown in FIG. 9. The end face shape of the hole machined by the forming beam is therefore steeper in the X direction than in the Y direction, and this shape is suitable for cross-section observation. Also, the ion beam current is increased compared with the case where control is performed so that both X and Y directions have a steep profile. If the stencil mask position is adjusted so that the ion beam irradiation axis overlaps with the cross-section position, and the rectangular hole end side of the stencil mask 57 overlaps with the irradiation axis, the skirt width of the beam can be controlled to be smaller. It is important here to ensure that the inclination direction of the axis along which the ion beam is extracted from the ion source is at least parallel to the machined surface to be observed. This is in order that the ion source inclination does not affect the cross-section formation to be observed. Also in this embodiment, to quantitatively deal with the steepness of the skirt shape of the beam profile, the skirt width of the beam profile was defined as the distance from 16% to 84% of the beam intensity (FIG. 9).

However, the steepness of the edge part of the beam spot may be defined other than by the skirt width, as in the second embodiment.

FIG. 11 shows a construction wherein an ion beam scanning deflection electrode is added at an intermediate position between the stencil mask 57 and the objective lens 55 of the ion beam system, and the sample is scanned by the beam to manufacture a cross-section. In this case, if the beam scanning direction is made to coincide with the direction parallel to the cross-section, efficient cross-section machining can be performed. Taking the case of the beam profile shown in FIG. 9 as an example, if the skirt shape of the beam profile is made steeper in the X direction than in the Y direction, it is important to set the rectangular area scanned by the beam by the central processing unit 95 so that the direction of at least one side in the beam scanning direction is parallel to the Y direction. If beam scanning is not performed, the machined shape is limited to the beam shape, but if ion beam scanning is performed, the beam machining shape will be flexible. There is also the advantage that the machining area can be set as desired beyond the beam shape.

Also, if a mechanism which limits the size of the mask hole in the stencil mask is provided, and the top of the sample is scanned by a forming beam projected through that hole to acquire a sample image and set the machining position, accurate positioning can be performed. The mechanism which limits the size of the mask hole may for example be a structure wherein a fine aperture is superimposed on the stencil mask. Also, in TEM sample production, if the same machining is performed from both sides of the surface to be observed, an identical effect can be obtained.

The machining procedure for obtaining a micro sample for TEM sample production is almost identical to the procedure shown in FIG. 6 of the first embodiment. Here, the beam shape is rectangular, and care must be taken that the final machining shape is unsymmetrical due to the skirt width of the beam being unsymmetrical in the X direction and the Y direction. In particular, the setting must be such that the direction perpendicular to the cross-section to be observed is the direction in which the skirt width of the beam profile becomes smaller. This can be implemented by system design.

In FIG. 6, at (a): First, an ion beam current of about 100 pA is prepared using a mask as a circular aperture. The two end marks 130 which form an observation cross-section are produced, and an observation position is pinpointed by the marks as in the first embodiment. Next, the mask is changed to a rectangular hole shape for rectangular hole machining. Here, a current of about 30 nA is obtained. Then, on the straight line connecting the two marks 130, the two rectangular holes 132 are formed on both sides of the marks 130 using the forming beam.

In FIG. 6, at (b): Next, the mask is changed over for thin, long trench machining.

In this change-over operation, the system user inputs a change-over command via the data input means. Here, the current acquired is about 10 nA. A thin long, perpendicular trench 133 is formed so that it intersects with one rectangular hole under this condition, and therefore does not intersect with the other rectangular hole. Also, in forming the thin, long perpendicular trench 133 in FIG. 6 at step (b), and forming the thin, long trench 135 in FIG. 6 at step (c), it is arranged that the direction perpendicular to a cross-section on the micro sample side of the thin, long perpendicular trench 133 and thin, long trench 135 is the direction in which the skirt of the beam profile is smaller. Here, from FIG. 6, step (c),—FIG. 6, step (d), the procedure of forming a wedge type micro sample and bringing the probe 137 into contact is the same as that of the first embodiment. Next, the system is changed over to a circular aperture and the current is adjusted to about 200 pA. This change-over operation can be performed also when the system user inputs a change-over command via the data input means. The probe 137 and sample 136 to be extracted are connected as in the first embodiment. Up to FIG. 6, steps (e), (f), (g), (h), (i), the operation is identical to that of the first embodiment.

At FIG. 6, step (j): Finally, membrane machining is performed. Here, the mask is changed over to a membrane machining mask. Specifically, rectangular masks are changed over so that the beam current decreases in the order roughing, intermediate machining and finishing. Finally, a thin finish is applied to produce a wall 143 with an observation area having a thickness of about 100 nm or less so as to give a TEM sample. Here, an example was described where the operator controls the system using the input unit of the central processing unit, but it is also possible to provide a memory means such as a memory in the central processing unit, and store the control conditions of all the steps as a control sequence so that sampling is fully automated.

After wall machining as described above, the micro sample is introduced into the TEM sample chamber. In TEM observation, cross-sections of defects and foreign matter can be observed with higher resolution than in SEM observation, and the cause of the defects can be analyzed in more detail from the observation results.

In this embodiment, the case was described where a double quadrupole lens was used as the non-axially symmetric ion beam lens to control the skirt width of the beam, but provided that non-axially symmetric control is possible, another quadrupole lens, an 8 pole lens or a 16 pole lens may be used. Combinations thereof, and combinations thereof with symmetric lenses, may also be used.

In the aforesaid embodiment, an argon ion beam was used, but it is clear that an identical effect can be obtained if another element such as nitrogen, oxygen, neon, xenon or krypton, or a mixed ion beam of these gases, is used.

In this embodiment, a non-axially symmetric ion beam lens was used to control the skirt width of the beam, but an aperture which makes the ion optical source shape non-axially symmetric and a symmetric ion beam lens may also be used. Specifically, the aperture through which ions are emitted from the ion source may be made elliptical or rectangular, or an identical non-axially symmetric aperture may be provided midway, and the lens adjusted using this aperture as the optical source. In this case also, the lens condition setting may be performed by the central processing unit. This will be described later.

Above, according to the sample manufacturing method or sample manufacturing device described in this embodiment, in addition to the effect of the sample manufacturing method or sample manufacturing device described in the first and second embodiments, neutral particles are removed, so metal neutral particles generated in the plasma ion source do not reach the sample, and even if the machined wafer is returned to the process, it very rarely causes defects. Also, as neutral particles of gas no longer extensively irradiate the sample, the machining of positions other than desired locations which would lead to sample deterioration no longer occurs.

Fourth Embodiment

In the sample manufacturing device having the construction shown in the third embodiment, neutral particles generated in the plasma ion source or neutral particles generated midway in the column do not reach the sample. However, ions of impurities such as metals generated in the plasma ion source do reach the sample. Hence, in this embodiment, a sample manufacturing device is described where a mass separator is installed midway in the ion beam path to trap ion impurities. In this embodiment also, a formed beam wherein the shape of the mask opening is projected on the sample, is used.

Figure 14:
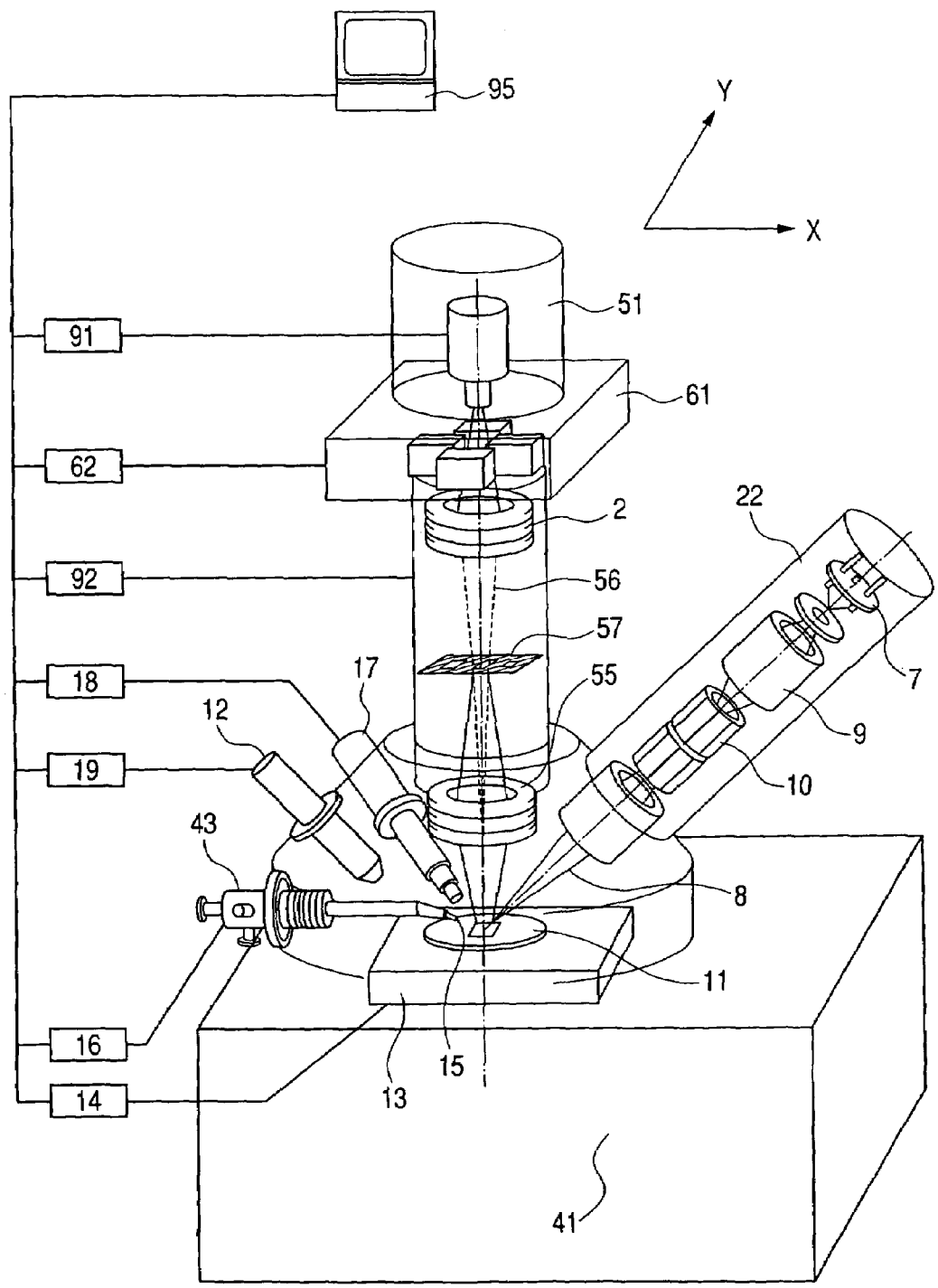
FIG. 14 is a diagram showing the overall appearance of an ion beam machining system according to a fourth embodiment.

FIG. 14 shows the ion beam machining system of this embodiment. The ion beam machining system of this embodiment comprises a vacuum chamber 41, this vacuum chamber 41 containing an ion beam irradiation system comprising a duoplasmatron 51, condenser lens 2, objective lens 55, stencil mask 57 and mass separator 61, together with the sample 11, secondary particle detector 12, sample stage 13, probe 15, precursor gas source 17 and manipulator 43. This system is controlled by a duoplasmatron controller 91, lens controller 92, sample stage controller 14, manipulator controller 16, precursor gas source controller 18, secondary electron detector controller 19, together with the mass separator controller 62 and central processing unit 95. Here, the central processing unit 95 is provided with a display which displays an image generated based on the detection signal of the secondary particle detector or data inputted by the data input means. Also, the sample stage comprises a linear transposition mechanism which transposes the sample directly in two directions in the plane of the sample mounting device, a linear transposition mechanism which transposes the sample in a direction perpendicular to the plane of the sample mounting device, a rotating mechanism in the plane of the sample mounting device and an inclination mechanism having an inclination axis in the plane of the sample mounting device, these controls being performed by a sample stage controller 14 on a command from the central processing unit 95. In the ion beam machining system of this embodiment, in addition to the ion beam irradiation system, an electron beam tube 22 is disposed which comprises an electron source 7, electron lens 9 and electron beam scanning deflector 10.

The operation of this device is essentially identical to that of the device of the first embodiment, but the mass separator is operated instead of the ion beam deflector to remove ions of impurities contained in the ion beam. The function of the mass separator is performed when the mass separator controller operates on a command from the central processing unit. The formed ion beam which has passed through the mass separator, condenser lens, mask and objective lens irradiates the sample and forms a rectangular hole. Subsequently, the sample cross-section can be observed by the electron beam emitted from the electron beam irradiation system.

To clarify the positional relationship between the construction of the mass separator and electron beam tower in the device of FIG. 14, and its relation to the cross-section forming direction, FIG. 15A shows the top surface, FIG. 15B shows the front surface and FIG. 15C shows the side surface of this system. FIGS. 15A to 15C also show the internal construction of the mass separator 61. In these figures, the secondary particle detector, precursor gas source and manipulator are omitted.

In the top surface view, front surface view and side surface view shown in FIGS. 15A to 15C, respectively, 1006 is the sample stage which holds the sample, 1001 is the ion source which generates the ion beam, 1002 is the irradiation optical system which irradiates the sample held in the sample stage by the ion beam, 1003 is the charged particle beam irradiation optical system for observing a cross-section machined by the ion beam, and 1010 is a mass separator. The mass separator 1010 of this embodiment is a so-called ExB mass separator wherein the electric field and magnetic field are respectively perpendicular to the ion beam, and the electric field and magnetic field are also perpendicular to each other 1012 is a permanent magnet, and 1011 is an electrostatic deflector for applying an electric field disposed in a direction perpendicular to the permanent magnet 1012. In this embodiment, a permanent magnet was used, but an electromagnet may be used instead. A mass separation using only a magnetic field may also be used. In this case, the ion beam path is refracted, but it is sufficient that a segment which is the projection of the mass dispersion direction of mass separation on the sample mounting surface of the stage is at least not parallel to the segment 1105 which is the projection of the irradiation axis of the charged particle beam used for observation on the sample mounting surface of the stage. The relation between the mass separation direction and column arrangement will be described later.

In the right-hand side of FIG. 15A, the arrow 1015 in the figure shows the direction in which mass dispersion occurs. Among ions which entered the mass separation device, only ions of a mass for which the magnetic field of the permanent magnet and the electric field are balanced, pass through a mass separation aperture 1013. However, it was found that the skirt width of the intensity profile of the projection beam is expanded by mass separation, and this was a hindrance to forming a steep cross-section. This is due to the fact that the energy of the ions, varies for each ion. When the ion beam is deflected by the ion beam deflector, a spread appears in the ion beam orbit in the deflection direction due to this energy difference. It was found that this effect extends also to the forming ion beam, and the skirt width is expanded in the direction of mass dispersion by the mass separation device. For this reason, in this device, the effect on the machining cross-section was avoided by arranging the mass separation device so that the mass dispersion direction of the mass separation device was not parallel to the machining direction in which a cross-section was tunneled. Hereafter, this will be described with reference to the left-hand side of FIG. 15A.

On the left-hand side of FIG. 15A, a segment 1106 is a segment which is the projection of the mass dispersion direction of the mass separation device 1010 on the sample mounting surface of the stage, and the segment 1105 is a segment which is the projection of the irradiation axis of the charged particle beam for machined cross-section observation on the sample mounting surface of the stage. An essential feature of the sample manufacturing device of this embodiment is that the segment 1105 and segment 1106 are not parallel.

If the segment 1105 and segment 1106 were parallel, the machined cross-section would be observed on the side where mass dispersion of the ion beam occurs, so a clear machined cross-section cannot be observed.

The machined cross-section can also be observed on the side where the sample stage is rotated and machined by the sharp side, but as the sample stage must be rotated, observation efficiency is poor and the sample piece manufacturing throughput therefore declines. By determining the correlation between the mass separator and charged particle beam irradiation optical system so that the segment 1105 and segment 1106 are not parallel, observation of the cross-section machined by the bluntest edge of the ion beam spot can be avoided. It is also preferred that the segment 1105 and segment 1106 are orthogonal to each other. This is because, if such an arrangement is adopted, the cross-section machined by the sharpest edge of the ion beam spot can be observed from the beginning. The relative positions of the segment 1105 and segment 1106 described above are the same even if the electron beam tube 22 of FIG. 14 and the mass dispersion direction of the mass separation device 61 are defined so that they are not mutually parallel. Therefore, due to the construction described with reference to FIG. 14, and FIG. 15A to 15C, a sharp cross-section can be formed in a short time by the forming ion beam, and the cross-section can be observed without rotating the sample stage after cross-section machining. Hence, high throughput cross-section observation can be performed by the electron beam.

In this embodiment, an axially symmetric lens was used for the condenser lens, but this can be substituted by a non-axially symmetric ion beam lens comprising a double quadrupole lens. Concerning the skirt width of the intensity profile of the rectangular ion beam projected on the sample, control is performed so that the width in the direction perpendicular to the sample cross-section to be observed, is less than in the direction perpendicular to the ion beam irradiation axis and parallel to the machined cross-section. The segment which is the projection of the mass dispersion direction of the mass separation on the sample mounting surface of the stage, is arranged to be at least parallel to the machined cross-section to be observed. The end face shape of the hole machined by the forming beam at this time is steeper in the X direction than in the Y direction, and is a suitable shape for cross-section observation. The ion beam current is large compared with the case where control is performed so that there is a steep profile in both the X and Y directions.

When an ion beam scanning deflection electrode is added to this ion beam machining device in an intermediate position between the stencil mask 57 and objective lens 55, and the sample is scanned by the beam to produce a cross-section, if the beam scanning direction coincides with the cross-section parallel direction, efficient cross-section machining can be performed.

Also, if a mechanism which limits the size of the mask hole in the stencil mask is provided, and the machining position is set by scanning the sample with the forming beam projected through this hole to obtain a sample image, a precise position setting can be performed. The mechanism which limits the size of the mask hole may for example be a structure which superimposes a fine aperture on the stencil mask.

In TEM sample production, if the same machining is performed from both sides of the surface to be observed, an identical effect can be obtained.

As for the machining procedure for micro sample production, this can be identical to the method shown in FIG. 5A to FIG. 5C.

To control the skirt width of the beam in this embodiment, a double quadrupole lens was taken as an example of a non-axially symmetric ion beam lens, but as long as non-axially symmetric control is possible, another quadrupole lens, an 8 pole lens or a 16 pole lens may also be used. Combinations thereof, and combinations thereof with symmetrical lenses, may also be used. Further, instead of a non-axially symmetric ion beam lens, an aperture which gives the ion optical source shape non-axial symmetry and a symmetrical ion beam lens may be used. Specifically, the aperture through which ions from the ion source are emitted can be made elliptical or rectangular, or a similar aperture with non-axial symmetry can be provided midway, and the lens adjusted by using this aperture as a light source. In this case also, the lens condition setup can be performed by the central processing unit. This is described later.

In this embodiment, although an argon ion beam was used, it is clear that the same effect can be obtained with elements, such as nitrogen, oxygen, neon, xenon, and krypton, and mixed ion beams thereof.

Also, in this embodiment, a duo plasma ion source was used, but even if a plasma ion source or liquid metal ion source using microwaves is used, an identical effect is obtained. In particular, if gold and impurities are removed from a gold silicon alloy with a mass separation device and the sample is irradiated with a silicon ion beam, in silicon device manufacture, the sample is not contaminated by impurities and a fine beam, which was difficult to obtain with a plasma ion source, can be obtained.

As described above, in the sample manufacturing method and sample manufacturing device described in this embodiment, in addition to the effect of the sample manufacturing method and sample manufacturing device described in the first to third embodiments, ions of impurities such as metal ions which are generated by the ion source are removed from the mass separator and do not reach the sample, and the sample is not contaminated with impurities, therefore the device manufacturing yield is not decreased.

Fifth Embodiment

In this embodiment, the case will be described where the skirt width of the ion beam intensity profile which irradiates the sample is formed with non-axial symmetry without inclining the ion beam.

In the third embodiment, a stencil mask was used for forming the cross-sectional shape of the ion beam, and a stencil mask is also used in this embodiment. The skirt width of the intensity profile of the ion beam which irradiates by the sample is controlled by an aperture disposed near the ion source. In this way, the skirt width of the intensity profile of the ion beam which irradiates the sample and the ion beam cross-sectional shape are controlled independently.

Figure 16:
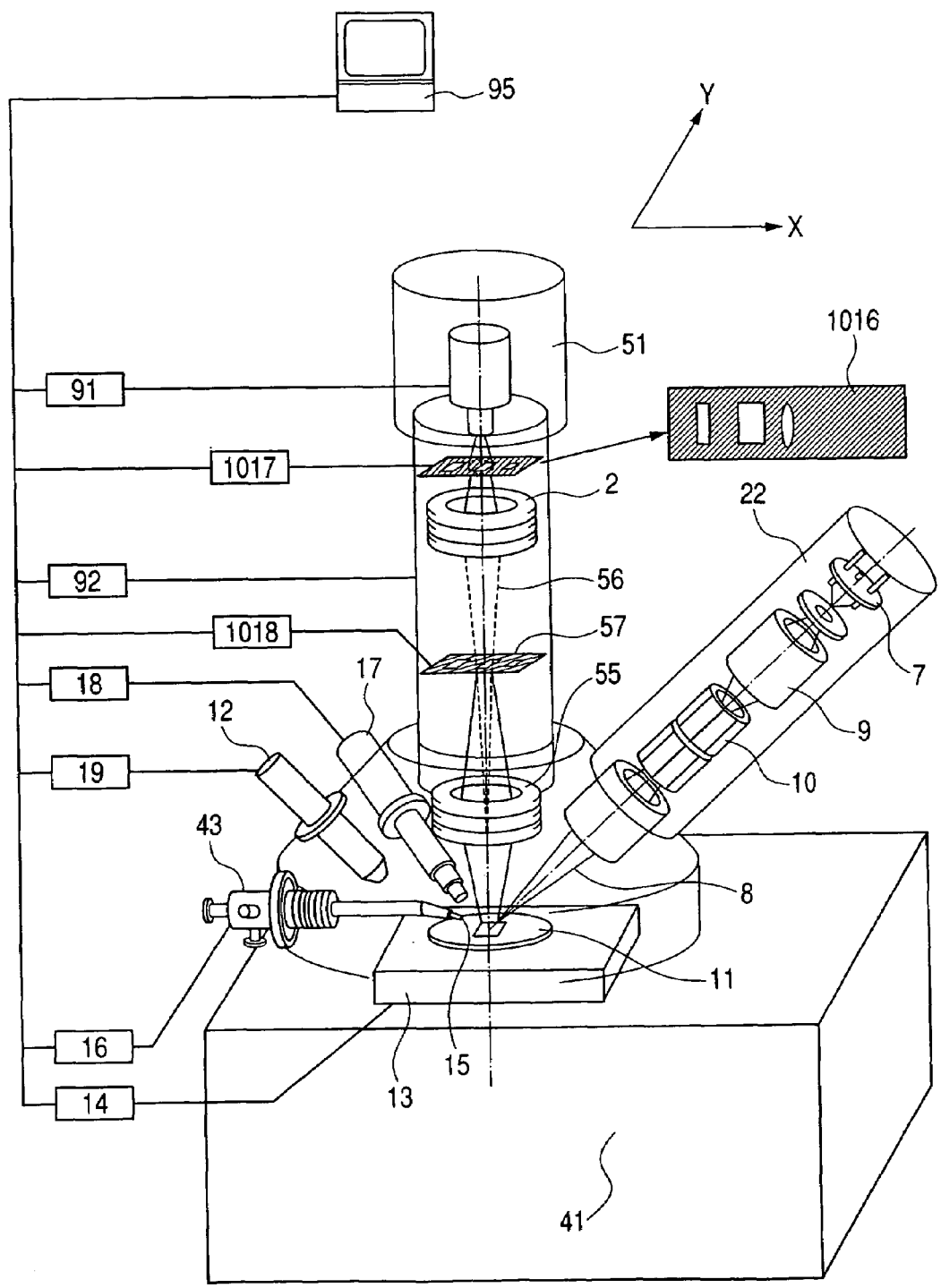
FIG. 16 is a diagram showing the overall appearance of an ion beam machining system according to a fifth embodiment.

FIG. 16 shows the ion beam machining system of this embodiment.

The ion beam machining device of this embodiment comprises a vacuum chamber 41, this vacuum chamber containing an ion beam irradiation system comprising a duoplasmatron 51, condenser lens 2, objective lens 55, stencil mask 57 and ion source aperture 1016, together with the sample 11, secondary particle detector 12, sample stage 13, probe 15, precursor gas source 17 and manipulator 43. The device which controls this system comprises the duoplasmatron controller 91, lens controller 92, sample stage controller 14, manipulator controller 16, precursor gas dispenser controller 18, secondary particle detector controller 19, and an ion beam aperture controller 1017, mask controller 1018 and the central processing unit 95.

The ion source aperture 1016 has plural openings, the opening shape being an ellipse, rectangle, square or circle.

Here, the central processing unit 95 is provided with a display which displays the image generated based on the detection signal of the secondary particle detector, and data input by a data input means. Also, the sample stage is provided with a linear transposition mechanism which transposes it directly in two directions in the sample mounting plane, a linear transposition mechanism which transposes it in a direction perpendicular to the sample plane, a mechanism which rotates it in the sample mounting plane, and an inclination mechanism which has an inclination axis in the sample mounting plane, these controls being performed by the sample stage controller 14 upon a command from the central processing unit 95.

An electron beam irradiation system comprising the electron gun 7, electron lens 9 and electron beam scanning deflector 10 is disposed in this device.

This device has an almost identical composition to that of the device of the first embodiment, but it is not provided with an ion beam deflector. The ion beam irradiated from the ion source passes through the ion source aperture 1016, condenser lens 2, stencil mask 57 and objective lens 55 to irradiate the sample. A machining hole is formed in a sample surface by the ion beam irradiation, and the machined cross-section in the sample is observed by the electron beam emitted by the electron beam irradiation system.

To clarify the positional relationship between the ion beam aperture and the electron beam tower in the system of FIG. 16, and FIGS. 17A to 17C show the top surface, front surface and side surface of this system, respectively. In these figures, the secondary particle detector, precursor gas source and manipulator are omitted. In the top surface, front surface and side surface shown in FIGS. 17A to 17C, respectively, 1006 is the sample stage which holds a sample, 1001 is the ion source which generates the ion beam and 1002 is the irradiation optical system which irradiates the sample held in the sample stage by the ion beam. In the ion beam irradiation system, two or more masks having desired openings are provided midway in the ion beam path, and the opening shape of at least one of the masks 57 is projected on the sample. The opening of the first mask, i.e., the ion source aperture 1016, has a non-axially symmetric shape, and the ion beam intensity profile projected on the sample also has a non-axially symmetric shape.

Figure 18:
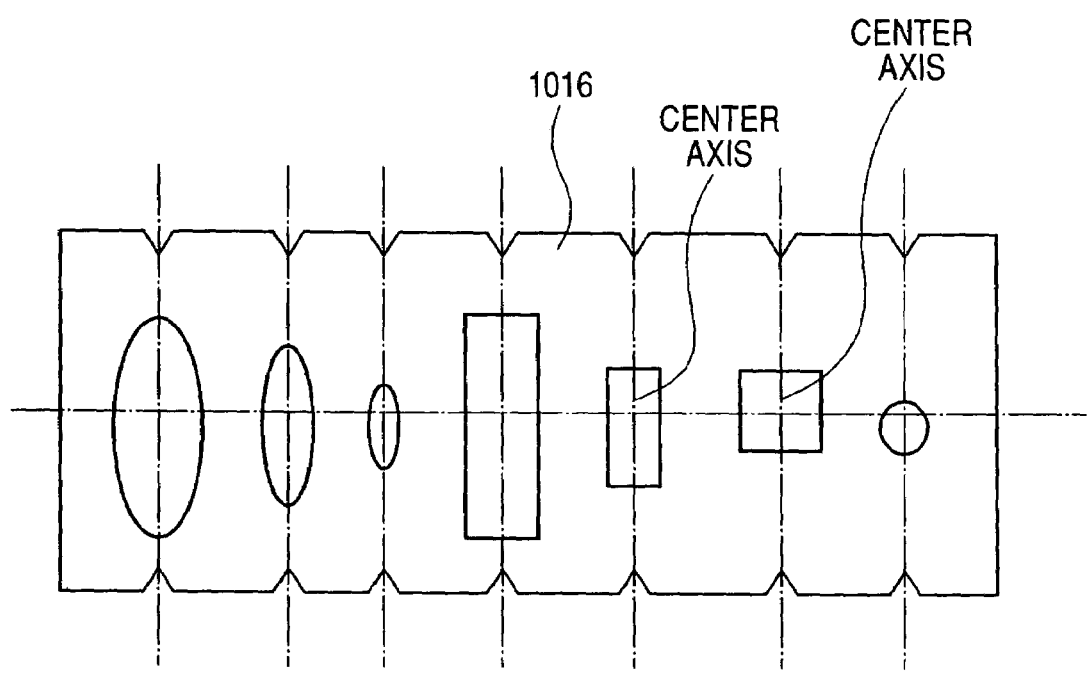
FIG. 18 is a diagram showing a typical construction of an ion beam-forming aperture.

FIG. 18 shows an example of the ion source aperture 1016 having a non-axially symmetric opening used in this embodiment. In the ion source aperture 1016, plural types of opening shapes are provided, these shapes being changed over according to the machining method.

For the sake of convenience during changeover, a notch is provided in each opening in the aperture end part. Although not shown in FIG. 16, in the machining device of the present embodiment, an ion source aperture feed mechanism is provided to select each opening by the notch. The dashed and dotted lines in the figure are respectively the center axes in the X direction and Y direction, and their intersection point forms the center axis of the opening. When an ion beam passes through the aperture, the beam center effectively passes along this axis. Here, "non-axially symmetrical shape" generally refers to any shape other than a circle, but in this application it also excludes a square shape. This is because, when the aperture shape is a square, the skirt width of the beam is identical in the X direction and Y direction.

Figure 17A:
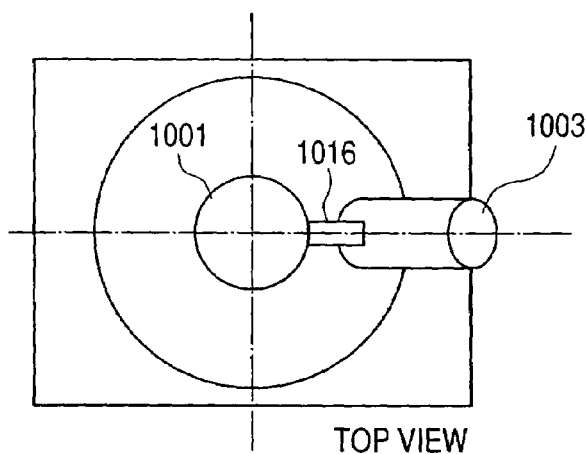
FIGS. 17A to 17C show cross-sectional views from the top, front and side of a machined cross-section of a sample machined by the ion beam machining system of the fifth embodiment.
Figure 17B:
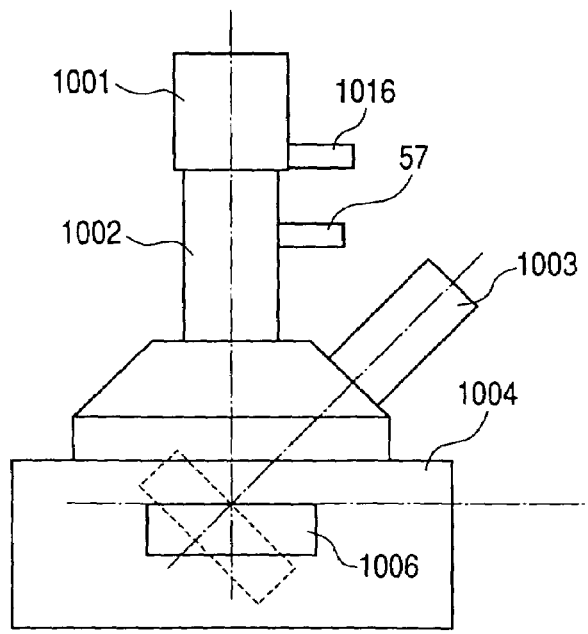
Figure 17C:
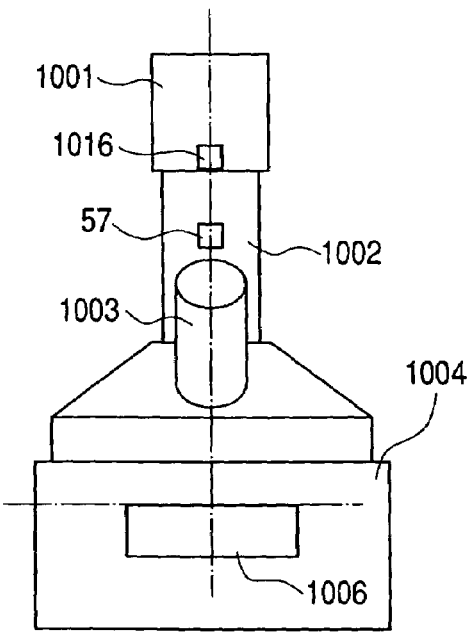
Figure 19A:
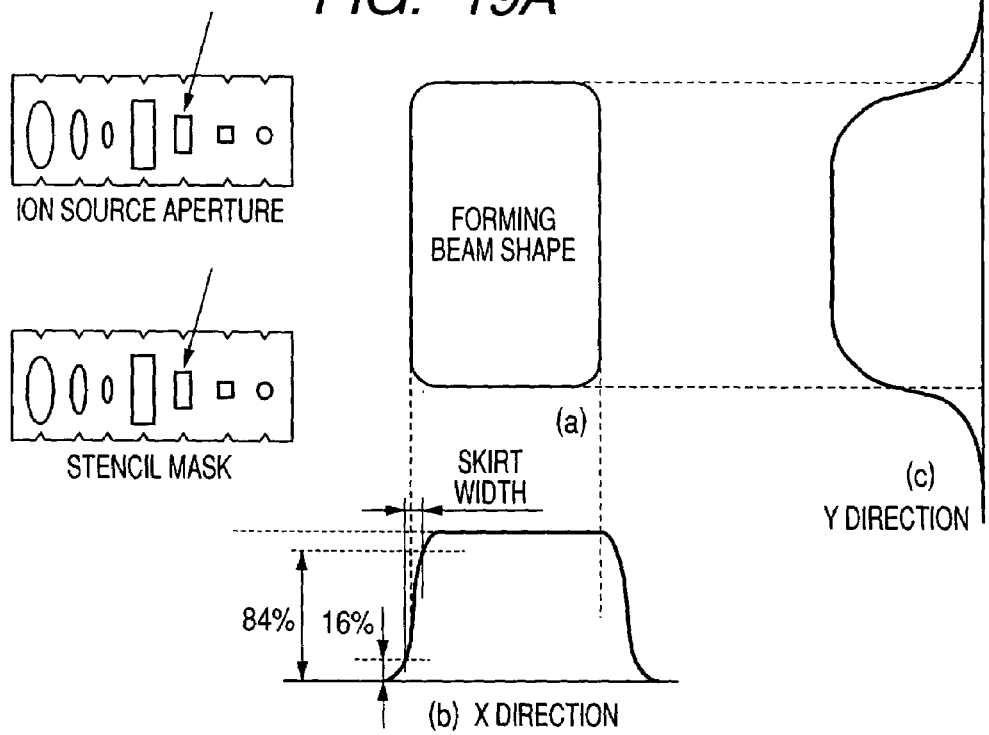
FIGS. 19A and 19B are diagrams illustrating an ion beam intensity profile, respectively, from the long axis and short axis directions.
Figure 19B:
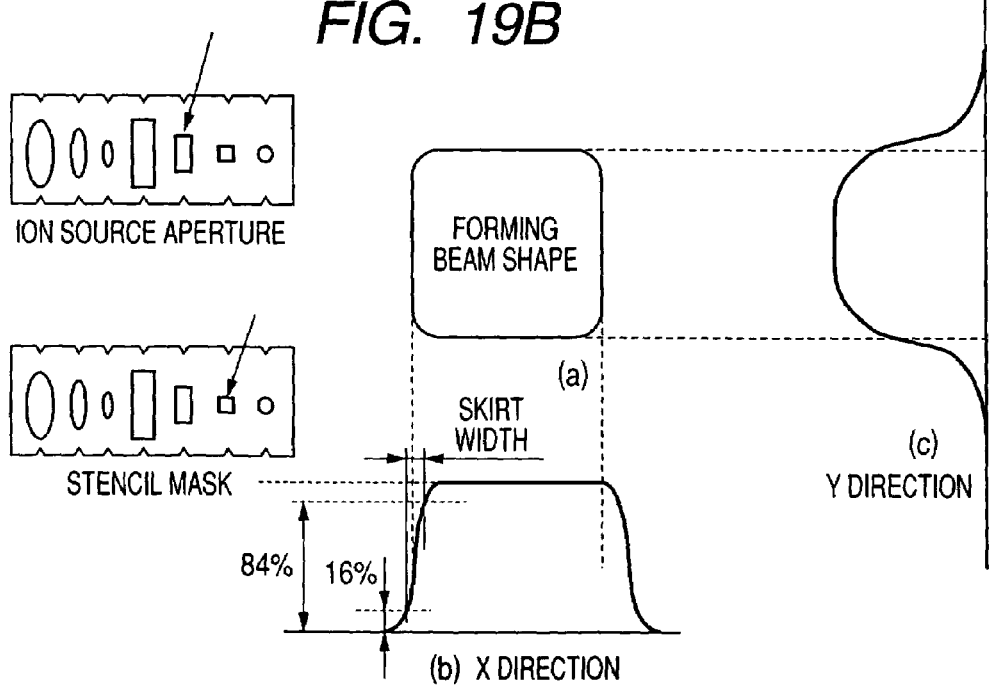

In this embodiment, inside the machining system, the ion source aperture of FIG. 18 is disposed so that the long axis direction of the opening coincides with the X direction of FIG. 17, and the short axis direction of the opening coincides with the Y direction of FIGS. 17A to 17C. If a setting is adopted wherein the long axis of the opening of the ion source aperture 1016, i.e., the rectangular shape or major diameter of the ellipse, coincides with the Y direction, the spread of the ion beam which passes through the objective lens is less in the X direction than in the Y direction, so the effect of aberration of the objective lens is reduced. Therefore, the skirt shape of the beam profile is steeper in the X direction than in the Y direction, and as a result, the end surface shape of the hole machined by the forming beam is steeper in the X direction than in the Y direction. The ion beam current is larger compared with the case where control is performed to give a steep profile in both the X and Y directions. In particular, if the stencil mask position is adjusted so that the rectangular hole end side of the stencil mask 57 is superimposed on the irradiation axis, the skirt width of the beam can be controlled to be smaller. This is because the aberration of the lens becomes a minimum on the ion beam irradiation axis. FIGS. 19A and 19B show the ion source aperture and the forming beam shape obtained by selecting the stencil mask and the beam profile. The selected aperture is indicated by an arrow in each figure. FIG. 19A shows a case where an ion source aperture with a rectangular opening and stencil mask with a rectangular opening are selected. The forming beam has a long intensity profile in the Y direction and a steep intensity profile in the X direction. FIG. 19B shows a case where an ion source aperture with a rectangular opening and a stencil mask with a square opening are selected. The forming beam is square, but it has a steep intensity profile in the X direction as seen in FIG. 19A. Thus, by choosing the ion source aperture, the skirt of the intensity profile can be controlled independently of the forming beam shape. In other words, the machining area setting and machining precision setting can be performed independently. According to this, as shown in FIG. 19B, a steep cross-section is formed in the X direction in the square area, and the plane of the machining hole is observed from the Y direction. Next, to enlarge the observation area for another region, the machining area in the Y direction is enlarged as seen in FIG. 19A, machining is performed with an identical specification as regards steepness, and observations are made in the same way from the Y direction. At this time, since only the plane which it is required to observe is machined steeply, the machining throughput increases, and by adopting an identical specification for the steepness of the cross-section, the observation area can be set freely.

As mentioned above, the feature of the device of this embodiment is that the ion beam irradiation system is a projection ion optical system comprising two or more masks having a desired opening midway in the ion beam path, which projects at least one of the mask shapes on the sample, and wherein the opening shape of the aperture mask is non-axially symmetric. In this construction, a segment which is the projection of the major axis direction on the sample mounting surface of the stage can be made at least perpendicular to a segment which is the projection of the irradiation axis of the electron beam irradiation optical system on the sample mounting surface of the stage. Due to this construction, a steep cross-section can be formed in a short time by the forming ion beam and the cross-section can be observed without rotating the sample stage after cross-section machining, so cross-section observation by the electron beam can be performed with high throughput. In this embodiment, although an argon ion beam was used, it is clear that the same effect can be obtained with elements such as nitrogen, oxygen, neon, xenon and krypton, and mixed ion beams thereof.

According to the present embodiment, an identical effect is obtained to that of the sample manufacturing method and sample manufacturing device described in the second embodiment. In the sample manufacturing device described in the second embodiment, the steepness of the ion beam profile was controlled using a non-axial symmetry ion beam lens, but it its adjustment was rather troublesome. However, in this embodiment, since the steepness of the ion beam profile is controlled by change-over of the ion beam aperture, its adjustment is simple.

Sixth Embodiment

In this embodiment, the case will be described of a converging ion beam system having a structure wherein, in addition to the impurity blocking function in the ion source due to the mass separator and the beam profile control function due to the inclined ion source arrangement described in the fourth embodiment, the ion beam column in which an inclined ion source is mounted, is itself inclined. In this embodiment, for convenience, the case where the skirt width of the ion beam is controlled using a non-axial symmetric aperture will be described, but the ion beam profile can also be formed using a stencil mask and plural non-axially symmetric apertures as described for the aforesaid embodiments.

In the device having the structure of the first to fourth embodiments, when the micro sample described in FIG. 6 is manufactured, the sample stage is inclined. However, when large wafers are handled, a considerable time was required to incline the stage. There was also the problem that the development of a large inclined stage was inherently difficult. Hence in this embodiment, the ion beam column is itself inclined to manufacture a micro sample by stage rotation without inclining the stage.

The appearance of the converging ion beam system of this embodiment is identical to that of the system shown in FIG. 14 except that the FIB column is inclined. Therefore, in this embodiment, the description using drawings of the whole device is omitted, and only a description using diagrams of essential parts will be given.

Figure 20A:
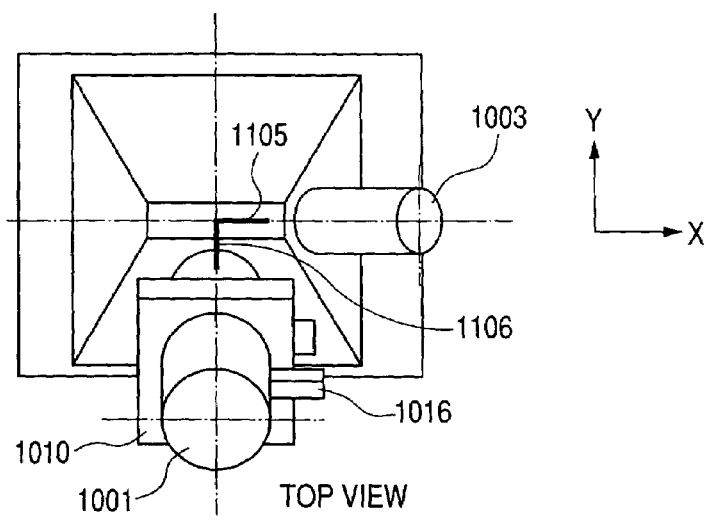
FIGS. 20A to 20C show a top view, plan view and side view of an ion beam machining system according to a sixth embodiment.
Figure 20B:
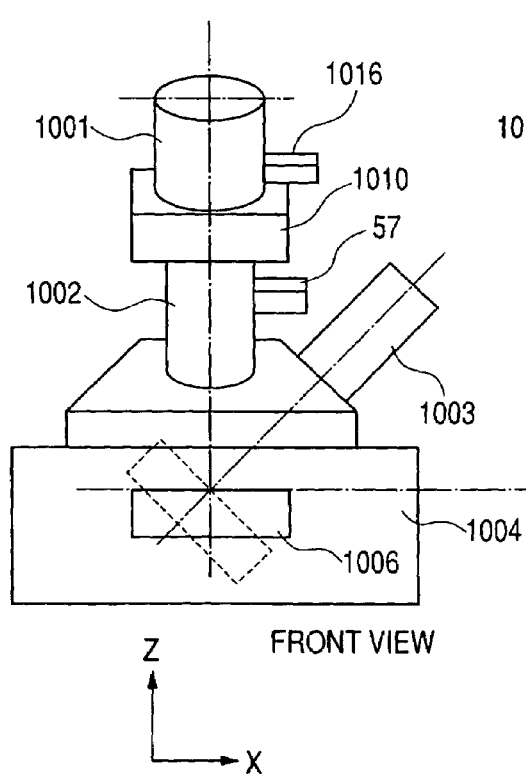
Figure 20C:
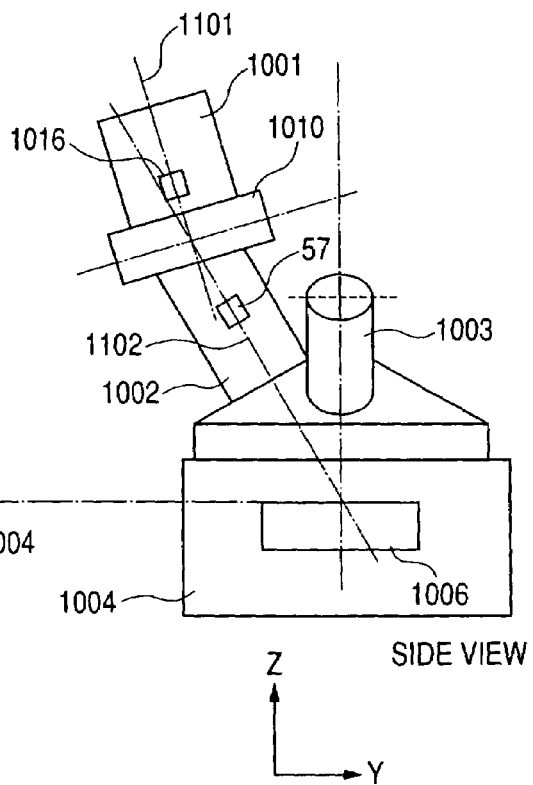

FIG. 20A-FIG. 20(c) show the top surface, front surface and side surface of the ion beam device of this embodiment. In the top surface, front surface and side surface, as respectively shown in FIG. 20A-FIG. 20(c), 1006 is the sample stage on which the sample is mounted, 1001 is the ion source which generates the ion beam, 1002 is the irradiation optical system, i.e., an ion beam column, which irradiates the sample held in the sample stage by the ion beam, and 1003 is the charged particle beam irradiation optical system, i.e., an SEM column, for observing the cross-section machined by the ion beam.

The internal structure of the ion beam irradiation system 1003 is essentially identical to the structure of the system shown in FIG. 16, wherein the ion source aperture 1016 and stencil mask 57 are disposed on the ion beam optical axis emitted from the ion source. The ion source aperture 1016 has a non-axially symmetric opening, the spot shape of the ion beam which passes through this aperture is formed with non-axial symmetry, and the stencil mask 57 projects the ion beam formed by the ion source aperture 1016 on the sample. Here, the segment 1105 is a segment which is the projection of the irradiation axis of the charged particle beam used for observation on the sample mounting surface of the sample stage, and 1106 is the segment which is the projection of the mass dispersion direction of the mass separator 1010 on the sample mounting surface of the sample stage.

Next, the inclination of the ion beam column 1002 to the SEM column 1003 will be described with reference to FIG. 20B and FIG. 20C. For convenience, the X and Y axes are taken in the plane of the sample stage, the Z axis is taken in the normal direction to the sample stage, and the center of the sample stage is taken as the origin of the sample system. In FIG. 20B, the SEM column 1003 is disposed at an inclination to the ZX plane, the inclination angle being 45° with respect to the Z axis. Likewise, in FIG. 20C, the ion beam column 1002 is disposed at an inclination to the YZ plane, the inclination angle being 60° with respect to the Y axis. 1101 is the extraction axis along which the ion beam is extracted from the ion source, and 1102 is the ion beam irradiation axis along which the ion beam irradiates the sample. Both 1101 and 1102 are inclined to the YZ plane, so the projection directions of 1101, 1102 on the sample stage are perpendicular to the segment 1105. By disposing the SEM column and the ion beam column in this way, and adjusting the mass separator 1010 so that the mass separation direction coincides with the segment 1106, the cross-section machined by the sharpest edge of the ion beam spot can be observed from the beginning. Also, the ion beam column and SEM column are disposed so that the segment 1105 and segment 1106 are at least not parallel. Alternatively, by adjusting the mass separator 1010, observation of the cross-section machined by the bluntest edge of the ion beam spot can be avoided.

The feature of the ion beam device of this embodiment is a structure wherein not only the ion source, but also the ion beam column is inclined. In the case of this structure, when a micro sample is manufactured by the ion beam, the micro sample can be manufactured by rotating the sample stage without inclining the stage, manufacturing throughput can be increased, and the micro sample can be manufactured even if the stage has no slanting degree of freedom.

In a system having this construction, when the long axis of the opening, i.e. the long side of the rectangle or the major axis of the ellipse of the ion beam aperture 1016 is aligned with the Y direction as shown in FIGS. 20A to 20C, the spread of the ion beam which passes through the objective lens is less in the X direction than in the Y direction, so the effect of the aberration of the objective lens is smaller. At this time, the skirt shape of the beam profile in the X direction is sharper than in the Y direction. Therefore, the shape of the end face of the hole machined by the forming beam is steeper in the X direction than in the Y direction, and the shape is suitable for cross-section observation. Also, the ion beam current is larger than if control were performed to give a steep profile in both the X and Y directions.

According to the sample manufacturing method and sample manufacturing device described in this embodiment, impurities such as metal ions generated by the ion source are removed from the mass separator and do not reach the sample, so the sample is not contaminated by impurities and device manufacturing yield does not decline. At the same time, neutral particles are removed and neutral particles of metals generated in the plasma ion source do not reach the sample, so even if a wafer is returned to the process after machining is complete, defects only rarely occur. Further, as neutral gas particles no longer extensively irradiate the sample, points other than desired locations are not machined, which would lead to sample deterioration. In addition to the sample manufacturing method or sample manufacturing device described in the first to fifth embodiments, a micro sample can be manufactured by the ion beam by rotating the sample stage without inclining the stage, so manufacturing throughput can be increased and the micro sample can be manufactured even if there is no degree of freedom in the inclination of the stage. Finally, the construction of a device which can handle large wafers is thereby simplified.

Seventh Embodiment

In accordance with the present invention, the following ion machining system and the ion beam machining method are described.

(1) An ion beam machining system which performs a predetermined machining by irradiating a sample with a converging ion beam, wherein the spot shape of the ion beam in a perpendicular plane with respect to the ion-beam-irradiation axis is non-axially symmetric, and machining is performed so that one of the cross-sections of the machined trenches formed on the sample is parallel to the short axis direction of the non-axially symmetric shape.

(2) An ion beam machining system which performs a predetermined machining by irradiating a sample with an ion beam, comprising a means for forming the beam spot shape in a perpendicular plane with respect to the ion beam irradiation axis to be non-axially symmetric, and a means for orienting one axis of the beam spot at the ion beam irradiation position in a predetermined direction.

(3) An ion beam machining device comprising a stage for mounting a sample to be machined, an ion beam column which irradiates or scans a sample by an ion beam, and an SEM column which irradiates the sample by an electron beam, wherein the ion beam column comprises a mass separator.

(4) A structure comprising a sample stage for holding a sample, an ion source which generates an ion beam, an irradiation optical source which forms an image of the ion optical source on the sample as a beam spot, a means which adjusts the shape of the beam spot to a non-axially symmetric shape to form the image, and a control means which, when the sample held on the sample stage is machined, arranges the machined cross-section of the sample and the long axis of the beam spot to be parallel, wherein the axis along which the ion beam is extracted from the ion source and the axis along which the ion beam irradiates the sample are inclined to each other, and wherein the segment which is the projection of this inclination direction on the sample mounting surface of the stage and the segment which is the projection of the long axis of the beam spot on the sample mounting surface of the stage are at least parallel to each other.

(5) An ion beam machining system comprising a sample stage for holding a sample, an ion source which generates an ion beam, a projection ion beam irradiation system which irradiates the sample by an ion beam extracted from the ion source through a mask having a hole of desired shape, and a control means which, controls the width of the skirt of the intensity profile of the rectangular ion beam projected on the sample in the direction perpendicular to the sample cross-section to be observed, to be less than that in the direction perpendicular to the ion beam irradiation axis and parallel to the machined cross-section, wherein the axis along which the ion beam is extracted from the ion source and the axis along which the ion beam irradiates the sample are inclined to each other, and the inclination direction is at least parallel to the machined cross-section to be observed.

(6) An ion beam machining system comprising a sample stage for holding a sample, an ion source which generates an ion beam, an irradiation optical system which irradiates the sample held in the sample stage by the ion beam, and a charged particle irradiation optical system for observing the cross-section machined by the ion beam, further comprising a mechanism for mass separation of the ion beam extracted from the ion source, wherein a segment which is the projection of the mass dispersion direction of mass separation on the sample mounting surface of the stage and a segment which is the projection of the irradiation axis of the charged particle beam used for observation on the sample mounting surface of the stage can be arranged to be at least orthogonal to each other.

(7) An ion beam machining system comprising a sample stage for holding a sample, an ion source which generates an ion beam, an irradiation optical system which forms an image of the ion optical source on the sample as a beam spot, a means which adjusts the shape of the beam spot to be non-axially symmetric to form the image, and control means which, when the sample held in the sample stage is machined, arranges the machined cross-section of the sample to be parallel to the long axis of the beam spot, further comprising a mechanism which mass separates the ion beam extracted from the ion source, wherein a segment which is the projection of the mass dispersion direction of mass separation on the sample mounting surface of the stage and a segment which is the projection of the long axis of the beam spot on the sample mounting surface of the stage are arranged to be at least parallel to each other.

(8) An ion beam machining system comprising a sample stage for holding a sample, an ion source which generates an ion beam, an irradiation optical system which irradiates the sample held in the sample stage by the ion beam, wherein this irradiation optical system forms an image of the ion optical source on the sample as a beam spot and its shape is adjusted to have non-axial symmetry, a control means which, when the sample held in the sample stage is machined, arranges the machined cross-section of the sample to the parallel to the long axis of the beam spot, and an irradiation optical system which irradiates the machined cross-section of the sample by a charged particle beam, wherein a segment which is a projection of this irradiation axis on the sample mounting surface of the stage can be arranged to be at least orthogonal to the long axis of the beam spot.

(9) An ion beam machining system comprising a sample stage for holding a sample, an ion source which generates an ion beam and an irradiation optical system which irradiates the sample held in the sample stage by the ion beam, wherein the ion beam irradiation system is a projection ion optical system comprising two or more masks having a desired opening midway in the ion beam path and at least one of the mask shapes is projected on the sample, the first mask has non-axial symmetry, and is arranged to be non-axially symmetric regarding the skirt of the intensity profile of the ion beam projected on the sample in the long axis direction and short axis direction.

(10) An ion beam machining system comprising a sample stage for holding a sample, an ion source which generates an ion beam and an irradiation optical system which irradiates the sample held in the sample stage by the ion beam, wherein a sample cross-section can be machined by this ion beam, the ion beam irradiation system is a projection ion optical system comprising two or more masks having a desired opening midway in the ion beam path wherein at least one mask shape is projected on the sample, at least one mask has non-axial symmetry, and by making its long axis direction parallel to the sample cross-section, the skirt width of the intensity profile of the ion beam projected on the sample is arranged to be smaller in the direction perpendicular to the sample cross-section to be observed, than in the direction perpendicular to the ion beam irradiation axis and parallel to the machined cross-section.

(11) An ion beam machining system comprising a sample stage for holding a sample, an ion source which generates an ion beam, an irradiation optical system which irradiates the sample held in the sample stage by the ion beam, wherein a sample cross-section can be machined by this ion beam, and a charged particle beam irradiation optical system for observing the cross-section machined by the ion beam, wherein the ion beam irradiation system is a projection ion optical system comprising two or more masks having a desired opening midway in the ion beam path and at least one mask shape is projected on the sample, at least one mask has a non-axially symmetric shape, and a segment which is a projection of its long axis direction on the sample mounting surface of the stage can be arranged to be at least perpendicular to a segment which is a projection of the irradiation axis of the charged particle beam irradiation optical system on the sample mounting surface of the stage.

(12) An ion beam machining system wherein the aforesaid ion source is a plasma ion source, and the aperture through which ions are extracted from the plasma is the aforesaid non-axially symmetric mask.

(13) The aforesaid ion beam machining system, wherein the non-axially symmetric shape is an ellipse.

(14) The aforesaid ion beam machining system, wherein the means used to adjust to an elliptical shape comprises an aperture having an elliptical or longitudinal opening, the system comprising an irradiation optical system which irradiates the machined cross-section of the sample by a charged particle beam, and wherein a segment which is a projection of its irradiation axis of the sample mounting surface of the stage can be arranged to be at least perpendicular to a segment which is a projection of the major axis of the ellipse or long side of the rectangle of the opening on the sample mounting surface of the stage.

(15) An ion beam machining method which forms a sample cross-section by an ion beam system comprising an ion source, an irradiation optical system which irradiates a sample by an ion beam extracted from the ion source, a sample stage which holds the sample and an ion beam control means which machines a sample cross-section, wherein the axis along which the ion beam is extracted from the ion source and the axis along which the ion beam irradiates the sample are inclined with respect to each other, the method comprising a step wherein the machined cross-section is observed by a charged particle beam from a direction in which a segment which is the projection of the inclination direction of the axis along which the ion beam is extracted from the ion source on the sample mounting surface of the stage and a segment which is the projection of the observation direction on the sample mounting surface of the stage, are perpendicular to each other.

(16) An ion beam machining method which forms a sample cross-section by an ion beam system comprising an ion source, an irradiation optical system which irradiates a sample by an ion beam extracted from the ion source, a sample stage which holds the sample and an ion beam control means which controls the ion beam to machine a sample cross-section, and further comprising a mechanism which mass separates the ion beam extracted from the ion source, the method comprising a step wherein the machined cross-section is observed by a charged particle beam from a direction in which a segment which is the projection of the mass dispersion direction of the mass separation mechanism on the sample mounting surface of the stage and a segment which is the projection of the observation direction on the sample mounting surface of the stage, are perpendicular to each other.

(17) An ion beam machining method which forms a sample cross-section by an ion beam system comprising an ion source, an irradiation optical system which irradiates a sample by an ion beam extracted from the ion source, a sample stage which holds the sample and an ion beam control means which controls the ion beam to machine a sample cross-section, comprising a step wherein the beam spot of the ion beam is adjusted to be non-axially symmetric by the irradiation optical system, a step wherein, when the sample held in the sample stage is machined, the sample cross-section and long axis of the beam spot are adjusted to be parallel, and a step wherein the machined cross-section is observed by a charged particle beam from a direction in which a segment which is the projection of the observation direction on the sample mounting surface of the stage is perpendicular to the long axis of the beam spot.

(18) The aforesaid ion beam machining method, wherein the ion beam is an ion beam formed by a projection ion irradiation system.

(19) The aforesaid ion beam machining method, wherein the forming ion beam is rectangular, and the method comprises a step wherein control is performed so that the skirt width of the intensity profile of the beam in the direction perpendicular to the machined cross-section to be observed, is less than in the direction perpendicular to the ion beam irradiation axis and parallel to the machined cross-section.

(20) The aforesaid ion beam machining method, wherein the ion beam comprises any one of an inert gas, oxygen or nitrogen as an element.

Eighth Embodiment

In accordance with the present invention, the following ion beam machining system is disclosed.

(1) An ion beam machining system comprising an ion source, a lens which converges an ion beam emitted from the ion source, a sample stage which holds the sample and an ion beam control means which controls the ion beam to machine a sample cross-section, and the system further comprises a control means which performs control so that at least one of the lenses which converges the ion beam is a lens which functions such that the aberrations in two directions perpendicular to the ion beam irradiation axis are different, and so that the relative positions of the sample held in the sample stage and the ion beam are such that the direction in which the aberration is the smaller of the two directions, faces the machined cross-section of the sample.

(2) An ion beam machining system comprising an ion source, two or more lenses which converge an ion beam emitted from the ion source, a sample stage which holds a sample and an ion beam control means which controls the ion beam to project a stencil mask on the sample to machine the sample cross-section, wherein at least one of the lenses which converges the ion beam has a different lens function in the two directions perpendicular to the ion beam irradiation axis, and the system further comprises a control means which performs control such that the lens function in the direction perpendicular to the machining cross-section and the direction perpendicular to the ion beam irradiation axis and parallel to the machining cross-section, are different.

(3) The aforesaid ion beam machining system, further comprising a control means which performs control so that, to observe the machined cross-section by the electron beam or ion beam, when a rectangular hole is formed in the sample by ion beam irradiation, the lens magnification in the direction perpendicular to the sample cross-section to be observed is less than in the direction perpendicular to the ion beam irradiation axis and parallel to the machined cross-section.

(4) The aforesaid ion beam machining system, further comprising a control means which performs control so that, to observe the machined cross-section by the electron beam or ion beam, the skirt width of the intensity profile of the rectangular formed ion beam projected on the sample in the direction perpendicular to the machined cross-section to be observed, is less than in the direction perpendicular to the ion beam irradiation axis and parallel to the machined cross-section.

(5) The aforesaid ion beam machining system, further comprising a mechanism which rotates the stencil mask around the ion beam irradiation axis as center.

(6) The aforesaid ion beam machining system, used to separate sample pieces machined by the ion beam from the sample.

(7) The aforesaid ion beam machining system, wherein the ion beam generated by the ion source comprises any one of an inert gas, oxygen or nitrogen as the element.

(8) An ion beam machining method for forming a sample cross-section by an ion beam system comprising an ion source, two or more lenses which converge the ion beam emitted from the ion source, an aperture through which the ion beam passes, a sample stage which holds a sample, and an ion beam control means which controls the ion beam to machine the sample cross-section, the method comprising a step wherein, in order to observe the machined cross-section by an electron beam or the ion beam, control is performed to form the cross-section so that the beam width in the direction perpendicular to the machined cross-section to be observed is less than the beam width in the direction perpendicular to the ion beam irradiation axis and parallel to the machined cross-section.

(9) The aforesaid ion beam machining method, comprising a step for rotating the aperture relative to the ion beam irradiation axis.

(10) An ion beam machining method, comprising a step for controlling an ion beam to project a stencil mask on a sample by ion beam machining system comprising an ion source, two or more lenses which converge the ion beam emitted from the ion source, a sample stage which holds a sample and a stencil mask so as to form a cross-section, wherein control is performed to form the cross-section so that at least one of the lenses which converges the ion beam has a different lens function in the direction perpendicular to the machined cross-section, and the direction perpendicular to the ion beam irradiation axis and parallel to the machined cross-section.

(11) The aforesaid ion beam machining method, comprising a step for performing control so that, to observe the machined cross-section by the electron beam or ion beam, when a rectangular hole is formed in the sample by ion beam irradiation, the lens magnification in the direction perpendicular to the machined cross-section to be observed is less than that in the direction perpendicular to the ion beam irradiation axis and parallel to the machined cross-section.

(12) The aforesaid ion beam machining method, comprising a step which performs control so that the skirt width of the intensity profile of the rectangular formed ion beam in the direction perpendicular to the machined cross-section to be observed, is less than in the direction perpendicular to the ion beam irradiation axis and parallel to the machined cross-section.

(13) The aforesaid ion beam machining method, comprising a step which rotates the stencil mask relative to the ion beam irradiation axis.

(14) The aforesaid ion beam machining method, wherein the ion beam contains any one of an inert gas, oxygen or nitrogen as the element.

(15) The aforesaid ion beam machining method, wherein the scanning direction of the ion beam is the direction parallel to the machined cross-section.

What is claimed is:

1. An ion beam system, characterized in comprising:
a sample stage holding a sample; and
an irradiation optical system which irradiates a sample held in this sample stage by an ion beam, wherein:
said irradiation optical system comprises means to adjust the beam spot shape of said ion beam to have non axial symmetry, and control means which arranges a machined surface of the sample parallel to the long axis of the beam spot when the sample held in said sample stage is machined.

2. The ion beam system according to claim 1, wherein the non-axial symmetry is that of an ellipse.

3. The ion beam system according to claim 2, wherein the ion beam system has an elliptical or rectangular aperture as means to adjust the beam spot shape to an ellipse.

4. The ion beam system according to claim 3, comprising a mechanism which rotates this aperture on the ion beam irradiation axis as center, and said control means controls the rotation of the rotating mechanism of said aperture so that the machined surface of said sample and the major axis direction of said beam spot are aligned parallel.

5. The ion beam system according to claim 1, wherein the rotating mechanism rotates said sample stage, and said control means controls the rotation of said sample stage so that the machined surface of said sample and the major axis direction of said beam spot are aligned parallel.

6. The ion beam system according to claim 1, comprising:
a detector which traps a charged particle beam secondarily generated from the sample due to said ion beam irradiation;
means to generate an image of said sample based on a detection signal of said detector;
a display which displays said generated image; and
input means which inputs required data to said control means.

7. The ion beam system according to claim 6, wherein said control means calculates a rotation angle of said aperture from coordinate data of machining area end points inputted via said input means and the detection signal of said detector, and transmits data concerning this rotation angle to said rotating mechanism.

8. The ion beam system according to claim 6, wherein said control means calculates a rotation angle of said aperture from position data of machining area end points inputted via said input means and the detection signal of said detector, and transmits data concerning this rotation angle to said rotating mechanism.

9. An ion beam system, comprising:
a sample stage holding a sample;
an ion source which generates an ion beam;
an irradiation optical system which irradiates a sample held in said sample stage by an ion beam;
a charged particle beam observation system for observing a surface machined by said ion beam;
and having a structure wherein an axis along which an ion beam is extracted from said ion source and an axis along which the sample is irradiated, are inclined to each other,
wherein a segment which is the projection of this inclination direction on the sample mounting surface of the stage, and a segment which is the projection of the irradiation axis of a charged particle beam for observation on the sample mounting surface of the stage, can be arranged to be at least perpendicular to each other.

10. The ion beam system according to claim 9, wherein said ion beam irradiation system is a projection ion beam irradiation system.

11. The ion beam system according to claim 9, comprising:
a detector which traps a charged particle beam secondarily generated from the sample by said ion beam irradiation;
means to generate an image of said sample based on the detection signal of said detector;
a display which displays the generated image; and
input means which inputs data required by said control means.

12. An ion beam system, comprising:
a sample stage holding a sample;
an ion source which generates an ion beam;
a projection ion beam irradiation system which irradiates the sample by the ion beam extracted from said ion source via a mask having an aperture of desired shape;
control means which controls the skirt width of the intensity profile of a square ion beam projected on the sample in the direction perpendicular to the sample cross-section to be observed, to be smaller than in the direction perpendicular to the ion beam irradiation axis and parallel to a machined cross-section; and
a mechanism which performs the mass separation of said ion beam extracted from said ion source,
wherein a segment which is the projection of the mass dispersion direction of mass separation on the sample mounting surface of said stage is at least parallel to the machined cross-section to be observed.

13. The ion beam system according to claim 12, wherein:
said control means which controls the skirt width of the intensity profile of the square ion beam projected on the sample in the direction perpendicular to the sample cross-section to be observed, to be smaller than in the direction perpendicular to the ion beam irradiation axis and parallel to a machined cross-section, includes control means which controls the lens magnification factor in the direction perpendicular to the sample cross-section to be observed, to be smaller than in the direction perpendicular to the ion beam irradiation axis and parallel to a machined cross-section.

14. The ion beam system according to claim 12, wherein:
said projection ion beam irradiation system is a projection ion optical system comprising two or more masks having a desired aperture in the ion beam path, and projects at least one mask shape on the sample,
wherein at least one mask has a shape with non-axial symmetry, and by making the long axis direction parallel to a sample cross-section, the skirt width of the intensity profile of the square ion beam projected on the sample in the direction perpendicular to the sample cross-section to be observed, is arranged to be smaller than in the direction perpendicular to the ion beam irradiation axis and parallel to a machined cross-section.

15. The ion beam system according to any of claims 9 through 14, wherein the ion beam system comprises a probe used when separating a sample piece machined by the ion beam from said sample.

16. The ion beam system according to any of claims 9 through 14, wherein the ion beam generated by said ion source contains any one of an inert gas, oxygen or nitrogen as an element.

* * * * *